(12) United States Patent
Zauderer et al.

(10) Patent No.: US 8,637,026 B2
(45) Date of Patent: Jan. 28, 2014

(54) ANTI-C35 ANTIBODY COMBINATION THERAPIES AND METHODS

(75) Inventors: Maurice Zauderer, Pittsford, NY (US); Elizabeth E. Evans, Bloomfield, NY (US)

(73) Assignee: Vaccinex, Inc., Rochester, NY (US)

( * ) Notice: Subject to any disclaimer, the term of this patent is extended or adjusted under 35 U.S.C. 154(b) by 399 days.

(21) Appl. No.: 12/810,743

(22) PCT Filed: Dec. 23, 2008

(86) PCT No.: PCT/US2008/013998
§ 371 (c)(1),
(2), (4) Date: Sep. 22, 2010

(87) PCT Pub. No.: WO2009/082485
PCT Pub. Date: Jul. 2, 2009

(65) Prior Publication Data
US 2011/0008322 A1    Jan. 13, 2011

Related U.S. Application Data

(60) Provisional application No. 61/016,763, filed on Dec. 26, 2007.

(51) Int. Cl.
*A61K 39/395* (2006.01)
(52) U.S. Cl.
USPC .................. 424/138.1; 424/141.1; 424/155.1
(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,474,893 A | 10/1984 | Reading |
| 4,647,447 A | 3/1987 | Gries et al. |
| 4,676,980 A | 6/1987 | Segal et al. |
| 4,687,659 A | 8/1987 | Quay |
| 4,714,681 A | 12/1987 | Reading |
| 4,716,111 A | 12/1987 | Osband et al. |
| 4,741,900 A | 5/1988 | Alvarez et al. |
| 4,816,567 A | 3/1989 | Cabilly et al. |
| 4,885,363 A | 12/1989 | Tweedle et al. |
| 4,925,648 A | 5/1990 | Hansen et al. |
| 4,946,778 A | 8/1990 | Ladner et al. |
| 4,994,560 A | 2/1991 | Kruper, Jr. et al. |
| 5,057,313 A | 10/1991 | Shih et al. |
| 5,120,525 A | 6/1992 | Goldenberg |
| 5,223,409 A | 6/1993 | Ladner et al. |
| 5,225,539 A | 7/1993 | Winter |
| 5,258,498 A | 11/1993 | Huston et al. |
| 5,274,119 A | 12/1993 | Frazier et al. |
| 5,314,995 A | 5/1994 | Fell, Jr. et al. |
| 5,342,604 A | 8/1994 | Wilson et al. |
| 5,367,080 A | 11/1994 | Toner et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,139 A | 6/1995 | Kiefer et al. |
| 5,435,990 A | 7/1995 | Cheng et al. |
| 5,441,050 A | 8/1995 | Thurston et al. |
| 5,474,981 A | 12/1995 | Leder et al. |
| 5,489,425 A | 2/1996 | Kruper, Jr. et al. |
| 5,505,931 A | 4/1996 | Pribish |
| 5,516,637 A | 5/1996 | Huang et al. |
| 5,516,717 A | 5/1996 | Hsu |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen et al. |
| 5,601,819 A | 2/1997 | Wong et al. |
| 5,625,126 A | 4/1997 | Lonberg et al. |
| 5,633,425 A | 5/1997 | Lonberg et al. |
| 5,652,361 A | 7/1997 | Simon et al. |
| 5,658,727 A | 8/1997 | Barbas et al. |
| 5,661,016 A | 8/1997 | Lonberg et al. |
| 5,677,171 A | 10/1997 | Hudziak et al. |
| 5,696,239 A | 12/1997 | Wilson et al. |
| 5,698,426 A | 12/1997 | Huse |
| 5,714,631 A | 2/1998 | Wilson et al. |
| 5,733,743 A | 3/1998 | Johnson et al. |
| 5,756,065 A | 5/1998 | Wilson et al. |
| 5,766,883 A | 6/1998 | Ballance et al. |
| 5,770,195 A | 6/1998 | Hudziak et al. |
| 5,772,997 A | 6/1998 | Hudziak et al. |
| 5,780,225 A | 7/1998 | Wigler et al. |
| 5,807,715 A | 9/1998 | Morrison et al. |
| 5,808,003 A | 9/1998 | Subramanian et al. |
| 5,814,318 A | 9/1998 | Lonberg et al. |
| 5,821,047 A | 10/1998 | Garrard et al. |
| 5,821,337 A | 10/1998 | Carter et al. |
| 5,837,242 A | 11/1998 | Holliger et al. |
| 5,876,969 A | 3/1999 | Fleer et al. |
| 5,885,793 A | 3/1999 | Griffiths et al. |
| 5,916,771 A | 6/1999 | Hori et al. |
| 5,935,801 A | 8/1999 | Schlossman et al. |

(Continued)

FOREIGN PATENT DOCUMENTS

DE   196 39 601 A1   9/1997
EP   0 071 564 A1    2/1983

(Continued)

OTHER PUBLICATIONS

Tuma (Oncology Times, 2003, p. 22).*

(Continued)

*Primary Examiner* — Laura B Goddard
(74) *Attorney, Agent, or Firm* — Alston & Bird LLP

(57) ABSTRACT

The present invention is directed to methods of killing cancer cells, the methods comprising administering at least one C35 antibody and either at least one HER2 or at least one EGFR antibody. In some embodiments, the antibodies are administered with a therapeutic agent. The present invention is further directed to C35, HER2 and EGFR antibodies useful in these methods.

14 Claims, 5 Drawing Sheets

(56) References Cited

U.S. PATENT DOCUMENTS

| | | | |
|---|---|---|---|
| 5,939,598 | A | 8/1999 | Kucherlapati et al. |
| 5,958,660 | A | 9/1999 | Taylor et al. |
| 5,969,108 | A | 10/1999 | McCafferty et al. |
| 5,972,622 | A | 10/1999 | Desjardins |
| 6,054,561 | A | 4/2000 | Ring |
| 6,071,491 | A | 6/2000 | Epstein et al. |
| 7,060,808 | B1 | 6/2006 | Goldstein et al. |
| 7,217,796 | B2 | 5/2007 | Wang et al. |
| 7,268,207 | B2 | 9/2007 | Zauderer et al. |
| 7,563,882 | B2 | 7/2009 | Zauderer et al. |
| 7,750,125 | B2 | 7/2010 | Zauderer et al. |
| 7,811,566 | B2 * | 10/2010 | Arakawa et al. ........... 424/143.1 |
| 2002/0018749 | A1 | 2/2002 | Hudson et al. |
| 2002/0052308 | A1 | 5/2002 | Rosen et al. |
| 2002/0123057 | A1 | 9/2002 | Zauderer et al. |
| 2003/0148409 | A1 | 8/2003 | Rossi et al. |
| 2004/0063907 | A1 * | 4/2004 | Zauderer et al. .............. 530/350 |
| 2005/0158323 | A1 | 7/2005 | Evans et al. |
| 2005/0196755 | A1 | 9/2005 | Zauderer et al. |
| 2005/0272637 | A1 | 12/2005 | Clinton et al. |
| 2007/0020261 | A1 | 1/2007 | Sliwkowski et al. |
| 2007/0037228 | A1 | 2/2007 | Moecks et al. |
| 2007/0081942 | A1 | 4/2007 | Zauderer et al. |
| 2007/0202516 | A1 | 8/2007 | Mass |
| 2007/0254295 | A1 | 11/2007 | Harvey et al. |
| 2008/0089886 | A1 | 4/2008 | Zauderer et al. |
| 2008/0305111 | A1 | 12/2008 | Evans et al. |
| 2009/0081210 | A1 | 3/2009 | Evans et al. |
| 2009/0297440 | A1 | 12/2009 | Zauderer et al. |
| 2009/0305350 | A1 | 12/2009 | Zauderer et al. |

FOREIGN PATENT DOCUMENTS

| | | | |
|---|---|---|---|
| EP | 0 232 751 | A1 | 8/1987 |
| EP | 0 396 387 | A2 | 11/1990 |
| EP | 0 439 095 | B1 | 7/1991 |
| EP | 0 592 106 | B1 | 4/1994 |
| WO | WO 89/00557 | A1 | 1/1989 |
| WO | WO 89/12624 | A2 | 12/1989 |
| WO | WO 91/09967 | A1 | 7/1991 |
| WO | WO 91/14438 | A1 | 10/1991 |
| WO | WO 92/06194 | A1 | 4/1992 |
| WO | WO 92/06204 | A1 | 4/1992 |
| WO | WO 92/08495 | A1 | 5/1992 |
| WO | WO 92/11018 | A1 | 7/1992 |
| WO | WO 93/11236 | A1 | 6/1993 |
| WO | WO 93/17715 | A1 | 9/1993 |
| WO | WO 93/21232 | A1 | 10/1993 |
| WO | WO 97/33899 | A1 | 9/1997 |
| WO | WO 97/34911 | A1 | 9/1997 |
| WO | WO 98/02543 | A1 | 1/1998 |
| WO | WO 98/50433 | A2 | 11/1998 |
| WO | WO 99/23105 | A1 | 5/1999 |
| WO | WO 00/55350 | A1 | 9/2000 |
| WO | WO 01/74859 | A2 | 10/2001 |
| WO | WO 01/78768 | A2 | 10/2001 |
| WO | WO 02/00677 | A1 | 1/2002 |
| WO | WO 03/104428 | A1 | 12/2003 |
| WO | WO 2004/008099 | A2 | 1/2004 |
| WO | WO 2005/055936 | A2 | 6/2005 |
| WO | WO 2007/076923 | A1 | 7/2007 |

OTHER PUBLICATIONS

Evans et al (Molecular Cancer Therapeutics, Nov. 2006, 5:2919-2930).*
Zimmerman et al (Drug Discovery Today, Jan. 2007, 12: 34-42).*
Pegram et al (J National Cancer Institute, 2004, 96:739-749).*
Stancovski et al (PNAS, 1991, 88:8691-8695).*
Evans, E., et al, "C35 is a novel immunotherapy target expressed in human breast and bladder carcinoma," *Breast Cancer Research and Treatment*, 2001, vol. 69(3), p. 311, Abstract Only.
Evans. E, et al., "C35 (*C17orf37*) is a novel tumor biomarker abundantly expressed in breast cancer," *Mol Cancer Ther*, 2006, vol. 5(11), pp. 2919-2930.
Fisher, D., et al., "Apoptosis in Cancer Therapy: Crossing the Threshold," *Cell*, 1994, vol. 78, pp. 539-542.
Friedman, L., et al., "Synergistic down-regulation of receptor tyrosine kinases by combinations of mAbs: Implications for cancer immunotherapy," *PNAS*, 2005, vol. 102(6), pp. 1915-1920.
Larbouret, C., et al., "In vivo Therapeutic Synergism of Anti-Epidermal Growth Factor Receptor and Anti-HER2 Monoclonal Antibodies against Pancreatic Carcinomas," *Clin Cancer Res*, 2007, vol. 13(11), pp. 3356-3362.
Lowe, S., et al., "p53-Dependent Apoptosis Modulates the Cytotoxicity of Anticancer Agents," *Cell*, 1993, vol. 74, pp. 957-967.
Perera, R., et al., "Treatment of Human Tumor Xenografts with Monoclonal Antibody 806 in Combination with a Prototypical Epidermal Growth Factor Receptor—Specific Antibody Generates Enhanced Antitumor Activity," *Clin Cancer Res*, 2005, vol. 11(17), pp. 6390-6399.
Spiridon, C., et al., "Targeting Multiple Her-2 Epitopes with Monoclonal Antibodies Results in Improved Antigrowth Activity of a Human Breast Cancer Cell Line in Vitro and in Vivo," *Clinical Cancer Research*, 2002, vol. 8, pp. 1720-1730.
"Researchers Find New Gene Associated with Breast Cancer," 2003, *Imaginis, The Women's Health Resource*, www.imaginis.com/breast-health-news/researchers-find-new-gene-associated-with-breast-cancer-dateline-august-31-2003.
Arnon, R., "Monoclonal Antibodies for Immunotargeting of Drugs in Cancer Therapy," *Monoclonal Antibodies and Cancer Therapy*, Reisfeld & Sell, eds., Alan R. Liss, Inc., New York, NY, 1985, pp. 243-256.
Berzofsky, J., et al., "Chapter 8: Immunogenicity and Antigen Structure," *Fundamental Immunology*, 1993, William E. Paul, ed., Raven Press, New York, p. 242.
Caldas, C., et al., "Humanization of the anti-CD18 antibody 6.7: an unexpected effect of a framework residue in binding to antigen," *Molecular Immunology*, 2003, vol. 39, pp. 941-952.
Casciola-Rosen, L., et al., "Autoantigens Tageted in Systemic Lupus Erythematosus Are Clustered in Two Populations of Surface Structures on Apoptotic Keratinocytes," *J. Exp. Med.*, 1994, vol. 179, pp. 1317-1330.
Chien, N., et al, "Significant structural and functional change of an antigen-binding site by a distant amino acid substitution: Proposal of a structural mechanism," *Proc. Natl. Acad. Sci. USA*, 1989, vol. 86, pp. 5532-5536.
Chowdhury, I., el al., "Current Concepts in Apoptosis: The Physiological Suicide Program Revisited," *Cellular & Molecular Biology Letters*, 2006, vol. 11, pp. 506-525.
Co, M., et al., "Humanized antibodies for antiviral therapy," *Proc. Natl. Acad. Sci. USA*, 1991, vol. 88, pp. 2869-2873.
Coldman, A., et al., "A Model for the Resistance of Tumor Cells to Cancer Chemotherapeutic Agents," *Mathematical Biosciences*, 1983, vol. 65, pp. 291-307.
Dadachova, E, et al., "Dead cells in melanoma tumors provide abundant antigen for targeted delivery of ionizing radiation by a mAb to melanin," *PNAS*, 2004, vol. 101(41), pp. 14865-14870.
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier," *Virology*, 1994, vol. 202, pp. 540-549.
Dillon, S., el al., "Annexin V Binds to Viable B Cells and Colocalizes with a Marker of Lipid Rafts upon B Cell Receptor Activation," *The Journal of Immunology*, 2000, vol. 164, pp. 1322-1332.
Fadok, V., el al., "Exposure of Phosphatidylserine on the Surface of Apoptotic Lymphocytes Triggers Specific Recognition and Removal by Macrophages," *The Journal of Immunology*, 1992, vol. 148(7), pp. 2207-2216.
Fell, H., et al., "Genetic Construction and Characterization of a Fusion Protein Consisting of a Chimeric F(ab') With Specificity for Carcinomas and Human IL-2," *The Journal of Immunology*, 1991, vol. 146(7), pp. 2446-2452.
Francis, M., et al., "Immunological Priming with Synthetic Peptides of Foot-and-Mouth Disease Virus," *J. Gen. Virol.*, 1985, vol. 66, pp. 2347-2354.

(56) References Cited

OTHER PUBLICATIONS

George, J., et al., "Differential Effects of Anti-$\beta_2$-Glycoprotein I Antibodies on Endothelial Cells and on the Manifestations of Experimental Antiphospholipid Syndrome," *Circulation*, 1998, vol. 97, pp. 900-906.

Giusti, A., et al., "Somatic diversification of S107 from an antiphosphocholine to an anti-DNA autoantibody is due to a single base change in its heavy chain variable region," *Proc. Natl. Acad. Sci. USA*, 1987, vol. 84, pp. 2926-2930.

Grand, R., et al., "A Novel Protein Expressed in Mammalian Cells Undergoing Apoptosis," *Experimental Cell Research*, 1995, vol. 218, pp. 439-451.

Greenspan, N., et al., "Defining epitopes: It's not as easy as it seems," *Nature Biotechnology*, 1999, vol. 17, pp. 936-937.

Guo, J., et al., "Recombinant Thyroid Peroxidase-Specific Fab Converted to Immunoglobulin G (IgG) Molecules: Evidence for Thyroid Cell Damage by IgG1, but Not IgG4, Autoantibodies," *Journal of Clinical Endocrinology and Metabolism*, 1997, vol. 82(3), pp. 925-931.

Güssow, D., et al., "Humanization of Monoclonal Antibodies," *Methods in Enzymology*, 1991, vol. 203, pp. 99-121.

Hammill, A., et al., "Annexin V Staining Due to Loss of Membrane Asymmetry Can Be Reversible and Precede Commitment to Apoptotic Death," *Experimental Cell Research*, 1999, vol. 251, pp. 16-21.

Hellström, K., et al., "Chapter 15—Antibodies for Drug Delivery,"*Controlled Drug Delivery*, 1987, Robinson, J.R. and Lee, V.H., eds, Marcel Dekker, Inc., New York, NY, pp. 623-653.

Higgins, B., et al., "Antitumor activity of crlotinib (OSI-774, Tarceva) alone or in combination in human non-small cell lung cancer tumor xenograft models," *Anti-Cancer Drugs*, 2004, vol. 15(5), pp. 503-512.

Jones, D. T., "Critically assessing the state-of-the-art in protein structure prediction," *The Pharmacogenomics Journal*, 2001, vol. 1, pp. 126-134.

Kettleborough, C., et al., "Isolation of tumor cell-specific single-chain Fv from immunized mice using phage-antibody libraries and the re-construction of whole antibodies from these antibody fragments," *Eur. J. Immunol.*, 1994, vol. 24, pp. 952-958.

Kishimoto, H., et al., "Upregulation of Surface Markers on Dying Thymocytes," *J. Exp. Med.*, 1995, vol. 181, pp. 649-655.

Koopman, G., et al., "Annexin V for Flow Cytometric Detection of Phosphatidylserine Expression on B Cells Undergoing Apoptosis," *Blood*, 1994, vol. 84(5), pp. 1415-1420.

Kostelny, S., et al., "Formation of a Bispecific Antibody by the Use of Leucine Zippers," *The Journal of Immunology*, 1992, vol. 148(5), pp. 1547-1553.

Lecoeur, H., et al., "Oncosis Is Associated With Exposure of Phosphatidylserine Residues on the Outside Layer of the Plasma Membrane: A Reconsideration of the Specificity of the Annexin V/Propidium Iodide Assay," *Cytometry*, 2001, vol. 44, pp. 65-72.

Mariuzza, R., et al., "The Structural Basis of Antigen-Antibody Recognition," *Ann. Rev. Biophy. Biophys. Chem.*, 1987, vol. 16, pp. 139-159.

Marupudi, N., et al., "Paclitaxel: a review of adverse toxicities and novel delivery strategies," *Expert Opin Drug Saf.*, 2007, vol. 6(5), pp. 609-621.

Morrison, Sherie L., "Transfectomas Provide Novel Chimeric Antibodies," *Science*, 1985, vol. 229, pp. 1202-1207.

Mueller, B., et al., "Serum half-life and tumor localization of a chimeric antibody deleted of the $C_H2$ domain and directed against the disialoganglioside GD2," *Proc. Natl. Acad. Sci. USA*, 1990, vol. 87, pp. 5702-5705.

Naramura, M., et al., "Mechanisms of cellular cytotoxicity mediated by a recombinant antibody-IL2 fusion protein against human melanoma cells," *Immunology Letters*, 1994, vol. 39, pp. 91-99.

Norton, L., et al., "Tumor Size, Sensitivity to Therapy, and Design of Treatment Schedules," *Cancer Treatment Reports*, 1977, vol. 61(7), pp. 1307-1317.

Rotello, R., et al., "Anti-apogens and anti-engulfens: monoclonal antibodies reveal specific antigens on apoptotic and engulfment cells during chicken embryonic development," *Development*, 1994, vol. 120, pp. 1421-1431.

Rudikoff, S., et al., "Single amino acid substitution altering antigen-binding specificity," *Proc. Natl. Acad. Sci. USA*, 1982, vol. 79, pp. 1979-1983.

Rüther, U., et al., "Easy identification of cDNA clones," *The EMBO Journal*, 1983, vol. 2(10), pp. 1791-1794.

Schipper, H., et al., "Shifting the Cancer Paradigm: Must We Kill to Cure?," *Journal of Clinical Oncology*, 1995, vol. 13(4), pp. 801-807.

Skolnick, J., et al., "From genes to protein structure and function: novel applications of computational approaches in the genomic era," *Trends in Biotechnology*, 2000, vol. 18, pp. 34-39.

Tam, James P., "Synthetic peptide vaccine design: Synthesis and properties of a high-density multiple antigenic peptide system," *Proc. Natl. Acad. Sci. USA*, 1988, vol. 85, pp. 5409-5413.

Thorpe, P., et al., "The Preparation and Cytotoxic Properties of Antibody-Toxin Conjugates," *Immunological Rev.*, 1982, vol. 62(1), pp. 119-158.

Thorpe, P. E., "Antibody Carriers of Cytotoxic Agents in Cancer Therapy: A Review," *Monoclonal Antibodies '84: Biological and Clinical Applications*, 1985, Pinchera, A., et al., eds., Editrice Kurtis, Milan, Italy, pp. 475-506.

Tosatto, S., et al., "Large-Scale Prediction of Protein Structure and Function from Sequence," *Current Pharmaceutical Design*, 2006, vol. 12, pp. 2067-2086.

Baselga, J., et al., "Phase II Study of Weekly Intravenous Recombinant Humanized Antio-p185$^{HER2}$ Monoclonal Antiobody in Patients With HER2/*neu*-Overexpressing Metastatic Breast Cancer," *J. Clin. Oncol. 14*:737-744, American Society of Clinical Oncology, United States (1996).

Brady, L.W., et al., "Malignant Astocytomas Treated with Iodine-125 Labeled Monoclonal Antibody 425 Against Epidermal Growth Factor Receptor: A Phase II Trial," *Int J Radiat Oncol Biol Phys 22*:225-230, Pergamon Press plc, United States (1991).

Chua, D.T.T., et al., "Prognostic Value of Epidermal Growth Factor Receptor Expression in Patients With Advanced Stage Nasopharyngeal Carcinoma Treated With Induction Chemotherapy and Radiotherapy," *Int J Radiat Oncol Biol Phys. 59*:11-20, Elsevier Inc., United Kingdom (2004).

Di Lorenzo, G., et al., "Expression of Epidermal Growth Factor Receptor Correlates with Disease Relapse and Progression to Andro-gen-independence in Human Prostate Cancer," *Clin Cancer Res. 8*:3438-3444, American Association for Cancer Research, United States (2002).

Faillot, T., et al., "A Phase I Study of an Anti-epidermal Growth Factor Receptor Monoclonal Antibody for the Treatment of Malignant Gliomas," *Neurosurgery 39*:478-483, Congress of Neurological Surgeons, United States (1996).

Fendly, B., et al., "Characterization of Murine Monoclonal Antibodies Reactive to Either the Human Epidermal Growth Factor Receptor or HER2/neu Gene Product," *Cancer Research 50*:1550-1558, American Association for Cancer Research, United States (1990).

Ko, H.-J., et al. "A Combination of Chemoimmunotherapies Can Efficiently Break Self-Tolerance and Induce Antitumor Immunity in a Tolerogenic Murine Tumor Model," *Cancer Res 67*:7477-7486, American Association for Cancer Research, United States, (2007).

Kopp, R., et al., "Reduced Survival of Rectal Cancer Patients With Increased Tumor Epidermal Growth Factor Receptor Levels," *Dis Colon Rectum 46*:1391-1399, The American Society of Colon and Rectal Surgeons, United States (2003).

Kull, F.C., et al., "Monoclonal Antibodies to Receptors for Insulin and Somatomedin-C," *J. Biol. Chem 258*:6561-6566, American Society for Biochemistry and Molecular Biology, United States (1983).

Li, S.L., et al., "Two New Monoclonal Antibodies Against the A Subunit of the Human Insulin-Like Growth Factor-I Receptor," *Biochem. Biophys. Res. Comm. 196*:92-98, Elsevier Inc., United Kingdom (1993).

Mendelsohn, J., "Epidermal Growth Factor Receptor Inhibition by a Monoclonal Antibody as Anticancer Therapy," *Clin Cancer Res. 3*:2703-2707, American Association for Cancer Research, United States (1997).

(56) References Cited

OTHER PUBLICATIONS

O-Charoenrat, P., et al., "Vascular endothelial growth factor family members are differentially regulated by c-*erb*B signaling in head and neck squamous carcinoma cells," *Clin. Exp. Metastasis 18*:155-161, Kluwer Academic Publishers, Germany (2000).

O-Charoenrat, P., et al., "Overexpression of Epidermal Growth Factor Receptor in Human Head and Neck Squamous Carcinoma Cell Lines Correlates With Matrix Metalloproteinase-9 Expression and In Vitro Invasion," *Int. J Cancer 86*:307-317, Wiley-Liss, Inc., United Kingdom (2000).

O-Charoenrat, P., et al., "The role of c-*erb*B receptors and ligands in head and neck squamous cell carcinoma," *Oral Oncol. 38*:627-640, Elsevier Science Ltd., United Kingdom (2002).

Pandini, G., et al., "Insulin and Insulin-like Growth Factor-I (IGF-I) Receptor Overexpression in Breast Cancers Leads to Insulin/IGF-I Hybrid Receptor Overexpression: Evidence for a Second Mechanism of IGF-I Signaling," *Clin Cancer Res. 5*:1935-1944, American Association for Cancer Research, United States (1999).

Pekonen, F., et al., "Receptors for Epidermal Growth Factor and Insulin-like Growth Factor I and Their Relation to Steroid Receptors in Human Breast Cancer," *Cancer Res. 48*:1343-1347, American Association for Cancer Research, United States (1998).

Peng, D., et al., "Anti-Epidermal Growth Factor Receptor Monoclonal Antibody 225 Up-Regulates $p27^{KIP1}$ and Induces $G_1$ Arrest in Prostatic Cancer Cell Line DU145," *Cancer Res. 56*:3666-3669, American Association for Cancer Research, United States (1996).

Ramos-Suzarte, M., et al., "$^{99m}$Tc-Labeled Antihuman Epidermal Growth Factor Receptor Antibody in Patients with Tumors of Epithelial Origin: Part III. Clinical Trials Safety and Diagnostic Efficacy," *J. Nucl. Med 40*:768-775, SNM, United States (1999).

Resnick, M.B., et al., "Epidermal Growth Factor Receptor, c-MET, β-Catenin, and p53 Expression as Prognostic Indicators in Stage II Colon Cancer," *Clin Cancer Res. 10*:3069-3075, American Association for Cancer Research, United States (2004).

Rodeck, U., et al., "Interactions Between Growth Factor Receptors and Corresponding Monoclonal Antibodies in Human Tumors," *J. Cell Biochem 35*:315-320, Alan R. Liss, Inc., United States (1987).

Selvaggi, G., et al., "Epidermal growth factor receptor overexpression correlates with a poor prognosis in completely resected non-small-cell lung cancer," *Ann Oncol. 15*:28-32, Oxford University Press, United Kingdom (2004).

Steller, M.A., et al., "Overexpression of the Insulin-like Growth Factor-1 Receptor and Autocrine Stimulation in Human Cervical Cancer Cells," *Cancer Res. 56*:1761-1765, American Association for Cancer Research, United States (1996).

Sturgis, E.M., et al., "Effects of antiepidermal growth factor receptor antibody 528 on the proliferation and differentiation of head and neck cancer," *Otolarynol. Head Neck Surg 111*:633-643, American Academy of Otolaryngology-Head and Neck Surgery Foundation, Inc., United States (1994).

Tsutsui, S., et al., "Prognostic and Predictive Value of Epidermal Growth Factor Receptor in Recurrent Breast Cancer," *Clin Cancer Res. 8*:3454-3460, American Association for Cancer Research, United States (2002).

Waterfield, M.D., et al., "A Monoclonal Antibody to the Human Epidermal Growth Factor Receptor," *J. Cell Biochem. 20*:149-161, Alan R. Liss, Inc., United States (1982).

Webster, N.J.G., et al., "Repression of the Insulin Receptor Promoter by the Tumor Suppressor Gene Product p53: A Possible Mechanism for Receptor Overexpression in Breast Cancer," *Cancer Res. 56*:2781-2788, American Association for Cancer Research, United States (1996).

Witton, C.J., et al., "Expression of the HER1-4 family of receptor tyrosine kinases in breast cancer," *J. Pathol. 200*:290-297, John Wiley & Sons, Ltd., United States (2003).

Xie, Y., et al., "Expression of Insulin-like Growth Factor-1 Receptor in Synovial Sarcoma: Association with an Aggressive Phenotype," *Cancer Res. 59*:3588-3591, American Association for Cancer Research, United States (1999).

International Search Report for International Application No. PCT/US08/13998, United States Patent and Trademark Office, United States, mailed on Feb. 23, 2009.

Written Opinion of the International Searching Authority for International Application No. PCT/US08/13998, United States Patent and Trademark Office, Alexandria, Virginia, mailed on Feb. 23, 2009.

\* cited by examiner

SEQUENCE LISTING

```
<160> NUMBER OF SEQ ID NOS: 10

<210> SEQ ID NO 1
<211> LENGTH: 354
<212> TYPE: DNA
<213> ORGANISM: Homo sapiens
<220> FEATURE:
<221> NAME/KEY: CDS
<222> LOCATION: (7)..(354)

<400> SEQUENCE: 1 gccgcg atg agc ggg gag ccg ggg cag acg tcc gta gcg ccc cct ccc      48
       Met Ser Gly Glu Pro Gly Gln Thr Ser Val Ala Pro Pro Pro
       1               5                   10 gag gag gtc gag ccg ggc agt ggg gtc cgc atc gtg gtg gag tac tgt    96
Glu Glu Val Glu Pro Gly Ser Gly Val Arg Ile Val Val Glu Tyr Cys
15                  20                  25                  30
```

| | | |
|---|---|---|
| gaa ccc tgc ggc ttc gag gcg acc tac ctg gag ctg gcc agt gct gtg<br>Glu Pro Cys Gly Phe Glu Ala Thr Tyr Leu Glu Leu Ala Ser Ala Val<br>35                         40                   45 | | 144 |
| aag gag cag tat ccg ggc atc gag atc gag tcg cgc ctc ggg ggc aca<br>Lys Glu Gln Tyr Pro Gly Ile Glu Ile Glu Ser Arg Leu Gly Gly Thr<br>50                        55                   60 | | 192 |
| ggt gcc ttt gag ata gag ata aat gga cag ctg gtg ttc tcc aag ctg<br>Gly Ala Phe Glu Ile Glu Ile Asn Gly Gln Leu Val Phe Ser Lys Leu<br>65                         70                   75 | | 240 |
| gag aat ggg ggc ttt ccc tat gag aaa gat ctc att gag gcc atc cga<br>Glu Asn Gly Gly Phe Pro Tyr Glu Lys Asp Leu Ile Glu Ala Ile Arg<br>80                         85                   90 | | 288 |
| aga gcc agt aat gga gaa acc cta gaa aag atc acc aac agc cgt cct<br>Arg Ala Ser Asn Gly Glu Thr Leu Glu Lys Ile Thr Asn Ser Arg Pro<br>95                       100               105               110 | | 336 |
| ccc tgc gtc atc ctg tga<br>Pro Cys Val Ile Leu<br>             115 | | 354 |

<210> SEQ ID NO 2
<211> LENGTH: 115
<212> TYPE: PRT
<213> ORGANISM: Homo sapiens

<400> SEQUENCE: 2

Met Ser Gly Glu Pro Gly Gln Thr Ser Val Ala Pro Pro Pro Glu Glu
1               5                   10                   15

Val Glu Pro Gly Ser Gly Val Arg Ile Val Val Glu Tyr Cys Glu Pro
                   20                   25                   30

Cys Gly Phe Glu Ala Thr Tyr Leu Glu Leu Ala Ser Ala Val Lys Glu
                 35                   40                   45

Gln Tyr Pro Gly Ile Glu Ile Glu Ser Arg Leu Gly Gly Thr Gly Ala
 50                  55                   60

Phe Glu Ile Glu Ile Asn Gly Gln Leu Val Phe Ser Lys Leu Glu Asn
65               70                   75                   80

Gly Gly Phe Pro Tyr Glu Lys Asp Leu Ile Glu Ala Ile Arg Arg Ala
                   85                   90                   95

Ser Asn Gly Glu Thr Leu Glu Lys Ile Thr Asn Ser Arg Pro Pro Cys
                 100               105               110

Val Ile Leu
       115

<210> SEQ ID NO 3
<211> LENGTH: 627
<212> TYPE: DNA
<213> ORGANISM: Mus sp.

<400> SEQUENCE: 3

| | |
|---|---|
| gaatttagcg gccgcgaatt cgcccttcga ctggagcacg ggacactgac atggactgaa | 60 |
| ggagtagaaa acatctctct cattagaggt tgatctttga ggaaaacagg gtgttgccta | 120 |
| aaggatgaaa gtgttgagtc tgttgtacct gttgacagcc attcctggta tcctgtctga | 180 |
| tgtacagctt caggagtcag gacctggcct cgtgaaacct tctcagtctc tgtctctcac | 240 |
| ctgctctgtc actggctact ccatcaccag tggttatttc tggaactgga tccggcagtt | 300 |
| tccagggaac aaactggaat ggatgggcta cataagctac gacggtagca ataactccaa | 360 |
| cccatctctc aaaaatcgaa tctccttcac tcgtgacaca tctaagaacc agttttttcct | 420 |
| gaagtttaat tctgtgacta ctgacgactc agctgcatat tactgtacaa aggaaactac | 480 |

```
ggggtttgct tactggggcc aagggactct ggtcactgtc tctgcagcca aaacgacacc      540
cccatctgtc tatccactgg ccctggatc tgctgcccaa actaactcca agggcgaatt      600
cgtttaaacc tgcaggacta gtcccctt                                        627
```

```
<210> SEQ ID NO 4
<211> LENGTH: 116
<212> TYPE: PRT
<213> ORGANISM: Mus sp.

<400> SEQUENCE: 4
```

```
Asp Val Gln Leu Gln Glu Ser Gly Pro Gly Leu Val Lys Pro Ser Gln
  1               5                  10                  15

Ser Leu Ser Leu Thr Cys Ser Val Thr Gly Tyr Ser Ile Thr Ser Gly
             20                  25                  30

Tyr Phe Trp Asn Trp Ile Arg Gln Phe Pro Gly Asn Lys Leu Glu Trp
         35                  40                  45

Met Gly Tyr Ile Ser Tyr Asp Gly Ser Asn Asn Ser Asn Pro Ser Leu
 50                  55                  60

Lys Asn Arg Ile Ser Phe Thr Arg Asp Thr Ser Lys Asn Gln Phe Phe
 65                  70                  75                  80

Leu Lys Phe Asn Ser Val Thr Thr Asp Ser Ala Ala Tyr Tyr Cys
                 85                  90                  95

Thr Arg Gly Thr Thr Gly Phe Ala Tyr Trp Gly Gln Gly Thr Leu Val
            100                 105                 110

Thr Val Ser Ala
            115
```

```
<210> SEQ ID NO 5
<211> LENGTH: 540
<212> TYPE: DNA
<213> ORGANISM: Mus sp.

<400> SEQUENCE: 5
```

```
cgcgaattcg ccttcgact ggagcacgag gacactgaca tggactgaag gagtagaaaa       60
attagctagg gaccaaaatt caaagacaga atggattttc aggtgcagat tttcagcttc      120
ctgctaatca gtgcctcagt cagaatgtcc agaggacaaa ttgttctcac ccagtctcca      180
gcaatcatgt ctgcatctcc aggggagaag gtcaccatat cctgcagtgc cagctcaagt      240
gtaagttaca tgaactggta ccagcagaag ccaggatcct ccccaaaacc ctggatttat      300
cacacatcca acctggcttc tggagtccct gctcgcttca gtggcagtgg gtctgggacc      360
tcttactctc tcacaatcag cagcatggag gctgaagatg ctgccactta ttactgccaa      420
cagtatcata gttacccacc cacgttcgga gggggggacca agctggaaat aaaacgggct      480
gatgctgcac caactgtatc catcttccca ccatccagtg agcaaagggc gaattcgttt      540
```

```
<210> SEQ ID NO 6
<211> LENGTH: 106
<212> TYPE: PRT
<213> ORGANISM: Mus sp.

<400> SEQUENCE: 6
```

```
Gln Ile Val Leu Thr Gln Ser Pro Ala Ile Met Ser Ala Ser Pro Gly
  1               5                  10                  15

Glu Lys Val Thr Ile Ser Cys Ser Ala Ser Ser Ser Val Ser Tyr Met
             20                  25                  30

Asn Trp Tyr Gln Gln Lys Pro Gly Ser Ser Pro Lys Pro Trp Ile Tyr
```

```
                35                    40                      45
His Thr Ser Asn Leu Ala Ser Gly Val Pro Ala Arg Phe Ser Gly Ser
    50                      55                      60

Gly Ser Gly Thr Ser Tyr Ser Leu Thr Ile Ser Ser Met Glu Ala Glu
65                      70                      75                      80

Asp Ala Ala Thr Tyr Tyr Cys Gln Gln Tyr His Ser Tyr Pro Pro Thr
                85                      90                      95

Phe Gly Gly Gly Thr Lys Leu Glu Ile Lys
            100                     105

<210> SEQ ID NO 7
<211> LENGTH: 618
<212> TYPE: DNA
<213> ORGANISM: Mus sp.

<400> SEQUENCE: 7
cgcgaattcg cccttcgact ggagcacgag gacactggac atggactgaa ggagtagaaa      60
atctctctca ctggaggctg attttttgaag aaggggttg tagcctaaaa gatgatggtg     120
ttaagtcttc tgtacctgtt gacagccctt ccgggtatcc tgtcagaggt gcagcttcag     180
gagtcaggac ctagcctcgt gaaaccttct cagactctgt ccctcacctg ttctgtcact     240
ggcgactcca tcaccagtgg ttactggaac tggatccgga aattcccagg aaataaactt     300
gaatacgtgg ggtacataag ctacagtggt ggcacttact acaatccatc tctcaaaagt     360
cgaatctcca tcactcgaga cacatccaag aaccactact acctgcagtt gaattctgtg     420
actactgagg acacagccac atattactgt gcaagaggtg cttactacgg gggggccttt     480
tttccttact tcgatgtctg gggcgctggg accacggtca ccgtctcctc agccaaaacg     540
acacccccat ctgtctatcc actggcccct ggatctgctg cccaaactaa ctccaagggc     600
gaattcgttt aaacctgc                                                   618

<210> SEQ ID NO 8
<211> LENGTH: 122
<212> TYPE: PRT
<213> ORGANISM: Mus sp.

<400> SEQUENCE: 8

Glu Val Gln Leu Gln Glu Ser Gly Pro Ser Leu Val Lys Pro Ser Gln
1               5                   10                      15

Thr Leu Ser Leu Thr Cys Ser Val Thr Gly Asp Ser Ile Thr Ser Gly
                20                  25                      30

Tyr Trp Asn Trp Ile Arg Lys Phe Pro Gly Asn Lys Leu Glu Tyr Val
            35                  40                      45

Gly Tyr Ile Ser Tyr Ser Gly Gly Thr Tyr Tyr Asn Pro Ser Leu Lys
        50                  55                      60

Ser Arg Ile Ser Ile Thr Arg Asp Thr Ser Lys Asn His Tyr Tyr Leu
65                  70                      75                      80

Gln Leu Asn Ser Val Thr Thr Glu Asp Thr Ala Thr Tyr Tyr Cys Ala
                85                  90                      95

Arg Gly Ala Tyr Tyr Gly Gly Ala Phe Phe Pro Tyr Phe Asp Val Trp
            100                 105                     110

Gly Ala Gly Thr Thr Val Thr Val Ser Ser
        115                 120

<210> SEQ ID NO 9
```

```
<211> LENGTH: 528
<212> TYPE: DNA
<213> ORGANISM: Mus sp.

<400> SEQUENCE: 9
gaattcgccc ttcccctgga gcacgaggac actgacatgg actgaaggag tagaaaatca      60
gttcctgcca ggacacagtt tagatatgag gttccaggtt caggttctgg ggctccttct     120
gctctggata tcaggtgccc actgtgatgt ccagataacc cagtctccat cttttcttgc     180
tgcatctcct ggagaaacca ttactattaa ttgcagggca agtaagtaca ttagcaaaca     240
tttagtctgg tatcaggaga aacctggaga aactaaaaag cttcttatct actctggatc     300
cactttgcaa tctggacttc catcaaggtt cagtggcagt ggatctggta cagatttcac     360
tctcaccatc agtagcctgg agcctgaaga ttttgcaatg tattactgtc aacagcataa     420
tgaatacccg ctcacgttcg gtgctgggac caagctggag ctgaaacggg ctgatgctgc     480
accaactgta tccatcttcc caccatccag tgagcaaagg gcgaattc                  528

<210> SEQ ID NO 10
<211> LENGTH: 107
<212> TYPE: PRT
<213> ORGANISM: Mus sp.

<400> SEQUENCE: 10

Asp Val Gln Ile Thr Gln Ser Pro Ser Phe Leu Ala Ala Ser Pro Gly
1               5                   10                  15

Glu Thr Ile Thr Ile Asn Cys Arg Ala Ser Lys Tyr Ile Ser Lys His
            20                  25                  30

Leu Val Trp Tyr Gln Glu Lys Pro Gly Glu Thr Lys Lys Leu Leu Ile
        35                  40                  45

Tyr Ser Gly Ser Thr Leu Gln Ser Gly Leu Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys
            100                 105
```

ANTI-C35 ANTIBODY COMBINATION THERAPIES AND METHODS

CROSS REFERENCE TO RELATED APPLICATIONS

This application is a U.S. National Phase application of International Application No. PCT/US2008/013998, filed Dec. 23, 2008, which claims priority to U.S. Provisional Appl. No. 61/016,763, filed Dec. 26, 2007, the entire contents of which are hereby incorporated by reference in their entirety.

REFERENCE TO A SEQUENCE LISTING SUBMITTED ELECTRONICALLY VIA EFS-WEB

This application includes a sequence listing, "sequence listing ascii.txt", 10,612 bytes, created on Sep. 21, 2010, submitted electronically via EFS-Web, which is incorporated herein by reference in its entirety.

BACKGROUND OF THE INVENTION

1. Field of the Invention

The present invention is directed to methods of killing cancer cells, particularly cancer cells that express C35. In one aspect, the method comprises administering at least one anti-C35 antibody and at least one anti-HER2 antibody. In another aspect, the method comprises administering at least one anti-C35 antibody and at least one anti-EGFR antibody. In some embodiments, a therapeutic agent is also administered in conjunction with the antibodies. In another aspect, the invention is directed to methods of designing a treatment for C35-positive cancers comprising testing for the expression of receptor molecules such as HER2, EGFR, and IGFR.

2. Background Art

Cell growth is a carefully regulated process which responds to specific needs of the body. Occasionally, the intricate and highly regulated controls dictating the rules for cellular division break down. When this occurs, the cell begins to grow and divide independently of its homeostatic regulation resulting in a condition commonly referred to as cancer. In fact, cancer is the second leading cause of death among Americans aged 25-44.

Current therapies for cancer include chemotherapy and radiation therapy. Chemotherapeutic drugs kill cancer cells mainly by inducing apoptosis (Fisher, D. E., *Cell* 78:539-542 (1994); Fung, C. Y., and D. E. Fisher, *J. Clin. Oncol.* 13:801-807 (1995); Lowe, S. W., et al., *Cell* 74:957-967 (1993)). Radiation therapy kills cancer cells by inducing apoptosis and by other mechanisms. However, chemotherapy and radiation therapy do not kill all cells in a given tumor, and cells that survive such treatment continue to grow. Thus, these treatments are often insufficient for eradicating an entire tumor. There is therefore a need for improved therapeutic methods of treating cancer.

Immunotherapeutic strategies for cancer have also been developed that target surface membrane markers differentially expressed in tumor cells using antibodies (e.g., U.S. Pat. No. 5,770,195, "Monoclonal Antibodies to the HER2 Receptor", Filed: May 23, 1995; Issued, Jun. 23, 1998). Many antigens differentially expressed in tumors are, however, not exposed on the surface of tumor cells. As a result, such intracellular antigens are not suitable as targets for antibody-based therapeutics.

BRIEF SUMMARY OF THE INVENTION

The present invention is directed to a method of killing cancer cells that express C35 and HER2, comprising administering to said cells: (a) an amount of an anti-C35 antibody or antigen binding fragment thereof that specifically binds C35; and (b) an amount of an anti-HER2 antibody or antigen binding fragment thereof that specifically binds HER2, wherein said amount of anti-C35 antibody and said amount of said anti-HER2 antibody is effective for killing said cancer cells. In one embodiment, the method further comprises administering an amount of a therapeutic agent. In one embodiment, the method is performed in vivo. In a further embodiment, the method is performed in a mammal, such as a human.

In one embodiment of the invention, the therapeutic agent is a chemotherapeutic agent. The chemotherapeutic agent is selected from the group consisting of cisplatin, carboplatin, paclitaxel, adriamycin, docetaxel, taxotere, gemcitabine, and vinorelbine. In one embodiment the chemotherapeutic agent is paclitaxel. In another embodiment the chemotherapeutic agent is adriamycin. In yet another embodiment the therapeutic agent is radiation.

In one embodiment of the invention, the therapeutic agent is administered prior to administering at least one of said anti-C35 antibody or said anti-HER2 antibody. In another embodiment, the therapeutic agent is administered after administering at least one of said anti-C35 antibody or said anti-HER2 antibody. In a further embodiment, the therapeutic agent is administered concurrently with at least one of said anti-C35 antibody or said anti-HER2 antibody. The anti-C35 antibody and anti-HER2 antibody are administered concurrently or sequentially. In one embodiment, each of the antibodies or fragments thereof is administered at a dose of about 0.1 mg/kg to about 100 mg/kg of a patient's body weight.

In one embodiment of the invention, the anti-C35 antibody or fragments is selected from the group consisting of 1F2, 1B3, MAbc0009, MAb 163, MAb 165, MAb 171, and variants or derivatives thereof that retain the binding specificity for C35. In another embodiment the anti-C35 antibody or fragment is 1F2 or a variant or derivative thereof that retains the binding specificity for C35. In a further embodiment the anti-C35 antibody or fragment is 1B3 or a variant or derivative thereof that retains the binding specificity for C35.

In one embodiment of the invention the anti-HER2 antibody is trastuzumab.

In one embodiment of the invention the cancer cells are selected from the group consisting of breast cancer, liver cancer, ovarian cancer, bladder cancer, lung cancer, prostate cancer, pancreatic cancer, colon cancer, and melanoma. In another embodiment the cancer cells are breast cancer cells. In a further embodiment, the breast cancer cells are intraductal carcinoma cells.

In one embodiment of the invention the method comprises administering more than one anti-C35 antibody or fragment thereof. In another embodiment, the method comprises administering more than one anti-HER2 antibody.

In one embodiment of the invention, the anti-C35 antibody is a humanized, chimeric, or human antibody. In another embodiment, the anti-HER2 antibody is a humanized, chimeric, or human antibody.

The present invention is also directed to a method of killing C35-positive cancer cells in a patient comprising testing for the expression of EGFR and HER2 in a sample of cancer cells of said patient; and administering an amount of an anti-EGFR antibody and an amount of an anti-C35 antibody effective to kill said cancer cells when said cancer cells are positive for EGFR expression; or administering an amount of an anti-HER2 antibody and an amount of an anti-C35 antibody effective to kill said cancer cells when said cancer cells are positive for HER2 expression. In one embodiment of the invention, EGFR or HER2 expression is determined by an in vitro assay.

In another embodiment, the in vitro assay is selected from the group consisting of immunohistochemistry (IHC), fluorescence in situ hybridization (FISH), polymerase chain reaction (PCR), and enzyme-linked immunosorbent assay (ELISA). In another embodiment, EGFR or HER2 expression is determined by an in vivo assay. In a further embodiment, EGFR or HER2 expression is determined by a cell imaging assay. EGFR and HER2 expression can be determined by different assay methods or the same assay method.

In one embodiment of the invention, the cancer is breast cancer. In a further embodiment, the breast cancer is an intraductal carcinoma. In yet another embodiment, the breast cancer is a breast cancer metastases.

In one embodiment of the invention, the anti-EGFR antibody is cetuximab. In another embodiment, the anti-HER2 antibody is trastuzumab.

In one embodiment of the invention, the anti-C35 antibody is 1B3 or a humanized variant or derivative thereof that retains binding specificity for C35. In another embodiment, the anti-C35 antibody is 1F2 or a humanized variant derivative thereof that retains binding specificity for C35. In a further embodiment, the anti-C35 antibody is fully human.

In one embodiment of the invention, the anti-EGFR antibody and said anti-C35 antibody are administered at different times. In another embodiment, the anti-EGFR antibody is administered before said anti-C35 antibody. In another embodiment, the anti-HER2 antibody and said anti-C35 antibody are administered at different times. In a further embodiment, the anti-HER2 antibody is administered before said anti-C35 antibody.

The present invention is also directed to a method of designing a treatment for a patient with a C35-positive cancer comprising testing for the expression of HER2 and EGFR in a biological sample from said cancer patient; selecting a combination antibody therapy comprising an anti-C35 antibody, and antibody against HER2 or EGFR, wherein an anti-HER2 antibody is selected when the biological sample is positive for HER2 expression and an EGFR antibody is selected when the biological sample positive for EGFR expression. In one embodiment, the biological sample is selected from the group consisting of tumor tissue, blood plasma, and blood serum.

In one embodiment of the invention, the C35-positive cancer is breast cancer. In another embodiment, the breast cancer is an intraductal carcinoma. In a further embodiment, the breast cancer is a breast cancer metastases.

In one embodiment of the invention, the anti-EGFR antibody is cetuximab. In another embodiment, the anti-HER2 antibody is trastuzumab. In a further embodiment, the anti-C35 antibody is 1B3 or a humanized variant or derivative thereof that retains binding specificity for C35. In yet another embodiment, the anti-C35 antibody is 1F2 or a humanized variant derivative thereof that retains binding specificity for C35. In another embodiment, the anti-C35 antibody is fully human.

The present invention is also directed to a method for identifying a patient that will respond therapeutically to a method of treating cancer with an antibody combination therapy comprising testing for the expression of C35, EGFR, and HER2 in a sample of cancer cells of said patient; determining the combination of C35, EGFR, HER2 expressed in said cancer cells; and providing a combination of antibodies against the combination of C35, EGFR and HER2 expressed in said cancer cells. In one embodiment of the invention, the cancer is selected from the group consisting of breast cancer, liver cancer, ovarian cancer, bladder cancer, lung cancer, prostate cancer, pancreatic cancer, colon cancer, and melanoma. In another embodiment, the cancer is breast cancer. In another embodiment, the breast caner is intraductal carcinoma.

In one embodiment of the invention, C35, EGFR, and HER2 expression is determined by an in vitro assay. In another embodiment, the in vitro assay is selected from the group consisting of immunohistochemistry (IHC), fluorescence in situ hybridization (FISH), polymerase chain reaction (PCR), and enzyme-linked immunosorbent assay (ELISA).

In one embodiment of the invention, EGFR or HER2 expression is determined by an in vivo assay. In another embodiment, EGFR or HER2 expression is determined by a cell imaging assay. In one embodiment, the cells express a combination of C35 and EGFR. In a further embodiment of the invention , the combination of antibodies comprises an anti-C35 antibody and an anti-EGFR antibody. In another embodiment, the cells express a combination of C35 and HER2. In another embodiment, the combination of antibodies comprises an anti-C35 antibody and an anti-HER2 antibody. In one embodiment, the cells express a combination of C35, EGFR, and HER2. In a further embodiment, the combination of antibodies provided is an anti-C35 antibody, an anti-EGFR antibody, and an anti-HER2 antibody.

In one embodiment of the invention, the method further comprises testing for the expression of IGFR in a sample of cancer cells of said patient; determining the combination of C35, EGFR, HER2, and IGFR expressed in said cancer cells; and providing a combination of antibodies against the combination of C35, EGFR, HER2, and IGFR expressed in said cancer cells. In another embodiment, the cells express a combination of C35 and IGFR. In a further embodiment, the combination of antibodies comprises an anti-C35 antibody and an anti-IGFR antibody.

The present invention is also directed to a method of killing cancer cells that express C35 and EGFR, comprising administering to said cells an amount of an anti-C35 antibody or antigen binding fragment thereof that specifically binds C35; and an amount of an anti-EGFR antibody or antigen binding fragment thereof that specifically binds EGFR, wherein said amount of anti-C35 antibody and said amount of said anti-EGFR antibody is effective for killing said cancer cells. In one embodiment the method further comprises administering an amount of a therapeutic agent. In another embodiment, the method is performed in vivo. In another embodiment, the method is performed in a mammal. In yet another embodiment, the mammal is a human.

In one embodiment of the invention, the therapeutic agent is a chemotherapeutic agent. In another embodiment, the chemotherapeutic agent is selected from the group consisting of cisplatin, carboplatin, paclitaxel, adriamycin, docetaxel, taxotere, gemcitabine, and vinorelbine. In one embodiment, the chemotherapeutic agent is paclitaxel. In another embodiment, the chemotherapeutic agent is adriamycin. In a further embodiment, the therapeutic agent is radiation.

In one embodiment, the therapeutic agent is administered prior to administering at least one of said anti-C35 antibody or said anti-EGFR antibody. In another embodiment, the therapeutic agent is administered after administering at least one of said anti-C35 antibody or said anti-EGFR antibody. In a further embodiment, the therapeutic agent is administered concurrently with at least one of said anti-C35 antibody or said anti-EGFR antibody.

In one embodiment of the invention, the anti-C35 antibody and said anti-EGFR antibody are administered concurrently. In another embodiment, the anti-C35 antibody and said anti-EGFR antibody are administered sequentially. In a further embodiment, each of the antibodies or fragments thereof is administered at a dose of about 0.1 mg/kg to about 100 mg/kg of a patient's body weight.

In one embodiment of the invention, the anti-C35 antibody or fragments is selected from the group consisting of 1F2, 1B3, MAbc0009, MAb 163, MAb 165, MAb 171, and variants or derivatives thereof that retain the binding specificity for C35. In another embodiment, the anti-C35 antibody or fragment is 1F2 or a variant or derivative thereof that retains the binding specificity for C35. In another embodiment, the anti-C35 antibody or fragment is 1B3 or a variant or derivative thereof that retains the binding specificity for C35. In a further embodiment, the anti-EGFR antibody is cetuximab.

In one embodiment of the invention, the cancer cells are selected from the group consisting of breast cancer, liver cancer, ovarian cancer, bladder cancer, lung cancer, prostate cancer, pancreatic cancer, colon cancer, and melanoma. In another embodiment, the cancer cells are breast cancer cells. In a further embodiment, the breast cancer cells are intraductal carcinoma cells.

In one embodiment of the invention, the method comprises administering more than one anti-C35 antibody or fragment thereof. In another embodiment, the method comprises administering more than one anti-EGFR antibody. In a further embodiment, the anti-C35 antibody is a humanized, chimeric, or human antibody. In yet another embodiment, the anti-EGFR antibody is a humanized, chimeric, or human antibody.

These and other aspects of the invention are described in further detail below.

DETAILED DESCRIPTION OF THE INVENTION

Overview

Figure 1:
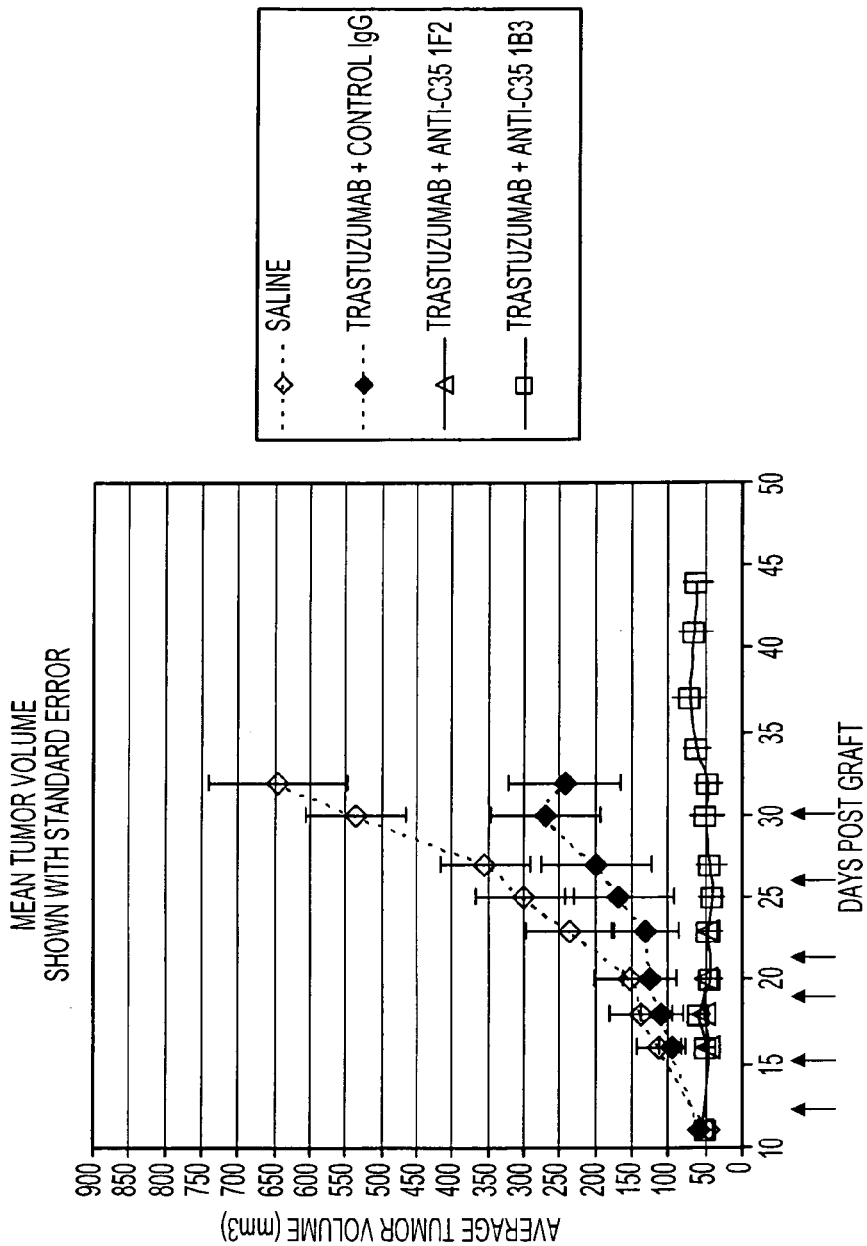
FIG. 1 shows the mean tumor volume of BT474-MD-grafted mice treated with trastuzumab+Control IgG, trastuzumab+anti-C35 1F2 antibody, trastuzumab+anti-C35 1B3 antibody, or Saline (treatment starting 12 days post-graft). Combinations of trastuzumab and either 1F2 or 1B3 anti-C35 antibodies significantly reduced tumor volume compared to trastuzumab alone. Arrows indicate treatment timepoints.

A number of studies have described alterations in the surface membrane of cells undergoing apoptosis. Prominent among these changes is the early loss of phospholipid asymmetry as reflected in the exposure of phosphatidylserine on the outer leaflet of the surface membrane. It has been reported that this alteration in surface membrane composition facilitates recognition and removal of apoptotic cells by macrophages (Fadok, V. A., et al., *J. Immunol.* 148:2207-2216 (1992)). A general method has been developed that allows detection of cells undergoing apoptosis by binding of the anticoagulant Annexin V to the exposed phosphatidylserine molecules (Koopman, G., et al., *Blood* 84:1415-1420 (1994)).

It has been determined that there is a subset of intracellular tumor-specific or tumor-associated antigens that become exposed on the tumor cell membrane under conditions of chemotherapy or radiation induced apoptosis and could be effective targets for concentrating antibody conjugated radioisotopes or toxins within the tumor. See US Appl. Publ. No. 2005/0158323 A1, published Jul. 21, 2005 (incorporated by reference herein in its entirety). In particular, the differentially-expressed tumor-specific C35 antigen that is normally associated with internal cell membranes becomes exposed on the surface membrane of tumor cells that have been induced to undergo apoptosis by radiation and/or chemotherapy. See US Appl. Publ. No. 2005/0158323 A1, FIGS. 1-3. Methods using antibodies against such antigens (e.g., C35) would be particularly effective because they could enhance the therapeutic benefits of standard apoptosis-inducing chemotherapy and radiation therapy in treating cancer. Likewise, other apoptosis-inducing agents, such as antibodies against surface-expressed cell signaling molecules (e.g., growth factor receptors such as HER2, EGFR, and/or IGFR), could be used to improve the therapeutic benefits of the antibodies against the intracellular antigens, e.g., antibodies against C35.

In one aspect, the present invention is directed to a method that, in one embodiment, acts in conjunction with the induction of apoptosis to enhance the eradication of tumors. It is based on the novel observation that a class of intracellular markers differentially expressed in tumor cells become exposed on the surface of apoptotic cells where they can be targeted by specific antibodies. In one aspect, apoptosis is induced by administering one or more antibodies against cell surface receptors such as EGFR, HER2, or IGFR. In a further aspect, one or more antibodies to the differentially expressed intracellular tumor antigen, e.g., C35, is administered. Such antibodies can be administered unconjugated or conjugated to a toxic payload. The benefits of this method of treatment are several-fold. For example, with conjugated antibodies, this method permits delivery to the tumor environment of a toxic payload that can destroy other non-apoptotic tumor cells in the vicinity of the apoptotic target. Also, by administering a combination of two or more antibodies, the antibodies may act synergistically, effectuating greater cell killing and allowing for lower doses or elimination of chemotherapeutic or radioactive therapies and thereby reducing the associated toxicity. Additionally, this method may prevent otherwise viable cells that have initiated the apoptotic process, for example, by treatment with an apoptosis-inducing agent, as evidenced by alterations in surface membrane constituents, from reversing the apoptotic progression and resuming growth (Hammill, A. K., et al., *Exp. Cell Res.* 251:16-21 (1999)).

Evans et al., reported that C35 is over-expressed in breast cancer, with 32% of grade 1 and 66% of grades 2 and 3 infiltrating ductal carcinomas of the breast testing positive for C35 expression. Evans et al., *Mol. Cancer Ther.* 5:2919-30 (November 2006) (incorporated by reference herein in its entirety). Because C35 expression is restricted in normal human tissue, see Evans et al., 2006, it is an excellent candidate for use as a biomarker and a diagnostic and therapeutic target, particularly in breast cancer.

Although normal cells proliferate by the highly controlled activation of growth factor receptor tyrosine kinases (RTKs) by their respective ligands, cancer cells also proliferate by the activation of growth factor receptors, but lose the careful control of normal proliferation. The loss of control may be caused by numerous factors, such as the overexpression of growth factors and/or receptors, and autonomous activation of biochemical pathways regulated by growth factors. Some examples of RTKs involved in tumorigenesis are the receptors for epidermal growth factor (EGFR), platelet-derived growth factor (PDGFR), insulin-like growth factor (IGFR), nerve growth factor (NGFR), and fibroblast growth factor (FGF). Binding of these growth factors to their cell surface receptors induces receptor activation, which initiates and modifies signal transduction pathways and leads to cell proliferation and differentiation.

Members of the epidermal growth factor (EGF) receptor family are particularly important growth factor receptor tyrosine kinases associated with tumorigenesis of epidermal cells. The first member of the EGF receptor family to be discovered was EGFR, which is expressed on many types of tumor cells. EGFR has been found to be involved in regulation of tumor cell division and growth, repair and survival, angiogenesis, invasion and tumor metastasis.

EGFR is a 170 kD membrane-spanning glycoprotein with an extracellular ligand binding domain, a transmembrane region and a cytoplasmic protein tyrosine kinase domain. Binding of specific ligands results in EGFR autophosphorylation, activation of the receptor's cytoplasmic tyrosine kinase domain and initiation of multiple signal transduction pathways that regulate tumor growth and survival. The EGFR pathway also influences production of various other angiogenic factors, such as VEGF and basis fibroblastic growth factor (bFGF), in tumors.

It has been reported that many human tumors express or overexpress EGFR. Expression of EGFR is correlated with poor prognosis, decreased survival, and/or increased metastasis. EGFR, because of this involvement in tumorigenesis, has been specifically targeted for anticancer therapies. These therapies have predominantly included either a monoclonal antibody that blocks binding of ligand to the extracellular domain of the receptor or a synthetic tyrosine kinase inhibitor that acts directly on the intracellular region to prevent signal transduction. Anti-EGFR antibodies also induce apoptosis in EGFR-positive tumor cells.

The insulin-like growth factors, also known as somatomedins, include insulin-like growth factor-I (IGF-I) and insulin-like growth factor-II (IGF-II) (Klapper, et al., *Endocrinol.* 112:2215 (1983); Rinderlmecht et al., *Febs. Lett.* 89:283 (1978)). These growth factors exert mitogenic activity on various cell types, including tumor cells (Macaulay *Br. J. Cancer* 65:311 (1992)), by binding to IGFR1 (Sepp-Lorenzino *Breast Cancer Research and Treatment* 47:235 (1998)). Interaction of IGFs with IGFR1 activates the receptor by triggering autophosphorylation of the receptor on tyrosine residues (Butler, et al., *Comparative Biochemistry and Physiology* 121:19 (1998)). Once activated, IGFR1, in turn, phosphorylates intracellular targets to activate cellular signaling pathways. This receptor activation is critical for stimulation of tumor cell growth and survival. Therefore, inhibition of IGFR1 activity represents a valuable potential method to treat or prevent growth of human cancers and other proliferative diseases. 100471 Several lines of evidence indicate that IGF-I, IGF-II and their receptor IGFR1 are important mediators of the malignant phenotype. Plasma levels of IGF-I have been found to be the strongest predictor of prostate cancer risk (Chan, et al., *Science* 279:563 (1998)) and similar epidemiological studies strongly link plasma IGF-I levels with breast, colon and lung cancer risk.

Another transforming gene was identified as a result of transfection studies with DNA from chemically induced rat neuroblastomas. This gene, originally called neu, was shown to be related to, but distinct from, the c-erbB proto-oncogene. By means of v-erbB and human EGFR as probes to screen human genomic and complementary DNA (cDNA) libraries, two other groups independently isolated human erbB-related genes that they called HER2 and c-erbB-2 respectively. Subsequent sequence analysis and chromosomal mapping studies revealed that c-erbB-2, and HER2 are species variants of neu.

HER2 is also a member of the tyrosine kinase family; and is closely related to, but distinct from, the EGFR gene as reported by Coussens et al., *Science* 230:1132 (1985). HER2 differs from EGFR in that it is found on band q21 of chromosome 17, as compared to band p11-p13 of chromosome 7, where the EGFR gene is located. Also, the HER2 gene generates a messenger RNA (mRNA) of 4.8 kb, which differs from the 5.8- and 10-kb transcripts for the EGFR gene. Finally, the protein encoded by the HER2 gene is 185,000 daltons, as compared to the 170,000-dalton protein encoded by the EGFR gene. Conversely, on the basis of sequence data, HER2 is more closely related to the EGFR gene than to other members of the tyrosine kinase family. Like the EGFR protein, the HER2 protein (p185) has an extracellular domain, a transmembrane domain that includes two cysteine-rich repeat clusters, and an intracellular kinase domain. Furthermore, amplification of the HER2 gene correlated significantly with the negative prognosis of the disease and the probability of relapse. Anti-HER2 antibodies, like anti-EGFR antibodies, induce apoptosis in tumor cells.

Others have observed that, with extracellularly expressed antigens such as HER2, administration of two different anti-HER2 antibodies directed to different epitopes of the protein resulted in anti-tumor activity in vivo and in vitro. Spiridon et al., Clin. Cancer Res. 8:1720-30 (2002) (incorporated by reference herein in its entirety). Indeed, synergistic effects have been demonstrated for administration of two different anti-HER2 antibodies (Spiridon, 2002; Friedman et al. *Proc. Natl. Acad. Sci USA* 102:1915-1920 (2005)); two different anti-EGFR antibodies (Friedman, 2005; Perera et al., *Clin. Cancer Res.* 11:6390-6399 (2005)); and a combination of one anti-HER2 and one anti-EGFR antibody (Larbouret et al., *Clin. Cancer Res.* 13:3356-3362 (2007)). These synergistic effects are the result of hypercrosslinking of the cell surface molecules by mixing high affinity antibodies directed against different epitopes on the same molecule (Spiridon, 2002). Since heterodimers are also formed between chains of HER2 and EGFR, crosslinking is also possible with one anti-HER2 and one anti-EGFR antibody. Simultaneous engagement of more than one epitope causes large aggregates of antibody-receptor complexes to form. These large aggregates are endocytosed faster than smaller antibody complexes which results in accelerated clearance of the receptors (Friedman, 2005). However, while Spiridon et al. observed an extracellularly expressed protein HER2, as described above, C35 is an intracellular antigen that becomes expressed on the cell surface in association with apoptosis. In one aspect, the present invention is directed to the use of anti-HER2 and/or anti-EGFR antibodies to induce cell surface expression of C35 to cause synergistic effects of anti-C35 antibodies and anti-HER2 and/or anti-EGFR antibodies.

The C35 gene is located on chromosome $17_q12$, and sits 505 nucleotides from the 3' end of the ERBB2 (Her2/neu) gene. (Evans et al., 2006). In one study, expression of C35 and HER2 was shown to correlate, with all HER2-positive breast tumors also testing positive for C35. (Evans et al., 2006). While as many as 50% of C35+ breast tumors also express HER2, and thus could be treated with a combination of C35 and HER2 antibodies, many C35+ tumors express low, or no HER2. As demonstrated in the Examples herein below, the majority of C35 positive tumors express either HER2 or EGFR, with a small subset of C35+ tumors expressing both HER2 and EGFR and a similar small subset expressing neither HER2 nor EGFR. As discussed above, both HER2 and EGFR are associated with tumor transformation and each is reported to induce apoptosis when targeted by antibodies. As demonstrated herein below, out of 30 analyzed tumors, 7/30 tumors were C35+/Her2+/EGFR−, 17/30 were C35+/Her2−/EGFR+, 3/30 were C35+/Her2+/EGFR+ and only 3/30 were C35+/Her2−/EGFR−. Thus, combination of C35 and HER2 or C35 and EGFR antibodies would be useful to treat tumors that are positive for these antigens (e.g., by inducing apoptosis to expose C35 on the surface, where it can be targeted with anti-C35 antibodies). The synergy of the HER2 and EGFR antibodies used in conjunction with anti-C35 antibodies is, at least in part due, to their causing cell surface exposure of C35. Also, the use of two antibodies could increase the receptor clearing activity, cell killing or other effector function of both molecules as opposed to treatments using either antibody individually. Therefore, in one aspect, the present invention is directed to methods for treating cancer, particularly breast cancer, comprising administering an amount of an anti-C35 antibody and an amount of an anti-HER2 antibody and/or an amount of an anti-EGFR antibody effective to kill the cancer cells.

I. Definitions

It is to be noted that the term "a" or "an" entity refers to one or more of that entity; for example, "a C35 antibody," is understood to represent one or more C35 antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of C35 and/or HER2 antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Variants of the antibodies include humanized versions of the antibodies as well as antibodies that have been affinity matured or optimized. Affinity optimization can be performed by routine methods that are well-known in the art. Alternatively, a preferred method for increasing the affinity of antibodies of the invention is disclosed in US 2002/0123057 A1. Derivatives of C35 and/or HER2 antibodies and antibody polypeptides of the present invention, are polypeptides which have been altered so as to exhibit additional features not found on the native polypeptide. Examples include fusion proteins. As used herein a "derivative" of a C35 and/or HER2 antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a C35, HER2 or EGFR antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). For example, two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to methods using certain anti-C35, anti-HER2 and anti-EGFR antibodies, or antigen-binding fragments, variants, or derivatives thereof. Unless specifically referring to full-sized antibodies such as naturally-occurring antibodies, the term "C35 antibodies", "HER2 antibodies" or "EGFR antibodies" (which is used interchangeably herein with the term "anti-C35 antibodies", "anti-HER2 antibodies" or "anti-EGFR antibodies", respectively) encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules. Likewise, the present invention is directed to methods using certain anti-IGFR1 antibodies, or antigen-binding fragments, variants, or derivatives thereof. Unless specifically referring to full-sized antibodies such as naturally-occurring antibodies, the term "IGFR antibodies" ((IGFR is used interchangeably herein with IGFR1 and IGFR antibodies is used interchangeably herein with the term "anti-IGFR antibodies") encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Also as used herein, the "antibodies of the invention" or "antibody polypeptides of the invention" include antibodies against C35, HER2, EGFR and IGFR, or C35, HER2, EGFR and IGFR polypeptide antibodies, respectively.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CO and the heavy chain ($C_H 1$, $C_H 2$ or $C_H 3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H 3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

Antibodies or antigen-binding fragments, variants, or derivatives thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by an Fab expression library, and anti-idiotypic (anti-Id) antibodies (including, e.g., anti-Id antibodies to C35 antibodies disclosed herein; also see, e.g., Hudson, P. J. and Couriau, C., Nature Med. 9: 129-134 (2003); U.S. Publication No. 20030148409; U.S. Pat. No. 5,837,242). ScFv molecules, for example, are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain C35, HER2 and/or EGFR or IGFR antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

Anti-C35, anti-HER2, anti-EGFR, or anti-IGFR antibodies, or antigen-binding fragments, variants, or derivatives thereof disclosed herein may be described or specified in terms of the epitope(s) or portion(s) of the antigen that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by the antibodies of the invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of C35, HER2, EGFR or IGFR.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ sec$^{-1}$, or $5 \times 10^6$ M$^{-1}$ sec$^{-1}$ or $10^7$ M$^{-1}$ sec$^{-1}$.

An antibody of the invention is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g. , Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

The antibodies for use in the invention may be "multispecific," e.g., bispecific, trispecific or of greater multispecificity, meaning that it recognizes and binds to two or more different epitopes present on one or more different antigens (e.g., proteins) at the same time. Thus, whether an antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an antibody of the invention, binding polypeptide or antibody. Each binding domain specifically binds one epitope. When a binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein in their entireties. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., *J. Immunol.* 148:1547-1553 (1992).

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat EA et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., C35 antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a C35, HER2 and/or EGFR antibody" and "an animal in need of treatment" includes subjects, such as mammalian subjects, that would benefit from administration of a C35, HER2 and/or EGFR antibody. As described in more detail herein, the antibodies of the invention can be used in unconjugated form or can be conjugated, e.g., to a drug, prodrug, or an isotope.

II. C35, HER2, EGFR and IGFR Target Polypeptides

C35 is an antigen differentially expressed in breast cancer and certain other tumor types including melanoma, colon carcinoma, ovarian cancer, hepatocellular carcinoma, bladder, and pancreatic cancer. The C35 protein has been shown to be prenylated and to associate with internal cell membranes but is not detectable on the surface membrane of viable tumor cells. There are a number of antibodies, including mouse monoclonal antibodies, humanized antibodies, and human antibodies, that immunospecifically recognize C35 epitopes. See US Appl. Publ. No. 2005/0158323 and U.S. pat. application Ser. No. 11/812,996 (incorporated herein by reference). The inventors have also demonstrated that induction of apoptosis in tumor cells by treatment either with a chemotherapeutic agent or irradiation results in surface membrane exposure of C35 that permits intact tumor cells to be recognized by C35-specific antibodies.

C35 Polynucleotide and amino acid sequences
(SEQ ID NOs: 1 and 2):

```
gccgcg atg agc ggg gag ccg ggg cag acg tcc gta
       Met Ser Gly Glu Pro Gly Gln Thr Ser Val
        1               5                   10 gcg ccc cct ccc gag gag gtc gag ccg ggc agt ggg
Ala Pro Pro Pro Glu Glu Val Glu Pro Gly Ser Gly
                15                  20 gtc cgc atc gtg gtg gag tac tgt gaa ccc tgc ggc
Val Arg Ile Val Val Glu Tyr Cys Glu Pro Cys Gly
            25                  30 ttc gag gcg acc tac ctg gag ctg gcc agt gct gtg
Phe Glu Ala Thr Tyr Leu Glu Leu Ala Ser Ala Val
 35              40                      45 aag gag cag tat ccg ggc atc gag atc gag tcg cgc
Lys Glu Gln Tyr Pro Gly Ile Glu Ile Glu Ser Arg
                50                  55 ctc ggg ggc aca ggt gcc ttt gag ata gag ata aat
Leu Gly Gly Thr Gly Ala Phe Glu Ile Glu Ile Asn
     60              65                      70 gga cag ctg gtg ttc tcc aag ctg gag aat ggg ggc
Gly Gln Leu Val Phe Ser Lys Leu Glu Asn Gly Gly
                 75                 80 ttt ccc tat gag aaa gat ctc att gag gcc atc cga
Phe Pro Tyr Glu Lys Asp Leu Ile Glu Ala Ile Arg
             85                 90 aga gcc agt aat gga gaa acc cta gaa aag atc acc
Arg Ala Ser Asn Gly Glu Thr Leu Glu Lys Ile Thr
 95                 100                    105 aac agc cgt cct ccc tgc gtc atc ctg tga
Asn Ser Arg Pro Pro Cys Val Ile Leu
                110             115
```

Recent cancer research has focused on the use of recombinant humanized monoclonal antibodies for the treatment of cancers whose cells overexpress HER2 or EGFR. Sequences of HER2 are known in the art and include, but are not limited to Genbank Accession Nos. NP_001005862, NP004439, AAA75493 or AAA35978. Sequences for EGFR are also known in the art and include, but are not limited to Genbank Accession Nos. AAB19486, AAH94761, AAI28420 and AAI18666. Lastly, nucleotide and amino acid sequence of a typical human IGFR precursor, include but are not limited to Genbank Accession No. X04434 or NM_000875, and those listed in U.S. Pat. No. 7,217,796. Cleavage of the precursor (e.g., between amino acids 710 and 711) produces an a-subunit and a n-subunit which associate to form mature IGFR.

The HER2 gene is closely related to, but distinct from, the gene encoding EGFR.

Amplification of the HER2 gene has been linked to neoplastic transformation in human breast cancer cells. Overexpression of HER2 has been identified within 20-30% of breast cancer patients, where it correlates with regionally advanced disease, increased probability of tumor recurrence, and reduced patient survival. As many as 30-40% of patients having gastric, endometrial, salivary gland, non-small cell lung, pancreatic, ovarian, peritoneal, prostate, or colorectal cancers may also exhibit overexpression of this protein. A small amount of HER2 protein is expressed on the plasma membrane of normal cells in a tissue-specific manner. This protein is present as part of a heterodimer receptor complex with other ERBB receptors that bind a growth factor ligand. Binding of this ligand activates the HER2 receptor, resulting in the transmission of growth signals from the outside of the cell to the nucleus. These growth signals regulate aspects of normal cell growth and division. Alterations of the HER2 gene in normal cells leads to overexpression of the HER2 protein, resulting in increased cell division, increased rate of cell growth, and may be associated with transformation to a cancer cell phenotype. When such alterations in the HER2 gene occur in tumor cells, either the HER2 protein is directly overexpressed, or gene amplification results in multiple copies of the gene and subsequent overexpression of the HER2 protein. The factor(s) triggering these alterations are unknown at present.

It has been demonstrated that overexpression of EGFR is also associated with poor survival and recurrences in colon (Resnick, M. B., et al., *Clin Cancer Res.* 10:3069-3075 (2004)), rectal (Kopp, R., et al., *Dis Colon Rectum* 46:1391-1399 (2003)), non-small-cell lung (Selvaggi, G., et al., *Ann Oncol.* 15:28-32 (2004)) and breast cancer (Witton, C. J., et al., *J Pathol.* 200:290-297 (2003); Tsutsui, S. et al., *Clin Cancer Res.* 8:3454-3460(2002)). It has also been suggested that EGFR expression status can identify a subgroup of patients within advanced nasopharyngeal carcinoma that will have a poor outcome after induction chemotherapy and radiotherapy (Chua, D. T. et al., *Int J Radiat Oncol Biol Phys.* 59:11-20 (2004)). There is evidence that expression of EGFR correlates with disease relapse and progression to androgen-independence in prostate cancer (Di Lorenzo, G. et al., *Clin Cancer Res.* 8:3438-3444 (2002)). Thus, detection of EGFR in clinical practice can influence patient management including questions of relevance of the use of EGFR-targeted drugs.

Overexpression of IGFR has also been demonstrated in several cancer cell lines and tumor tissues. IGFR is overexpressed in 40% of all breast cancer cell lines (Pandini, et al., *Cancer Res.* 5:1935 (1999)) and in 15% of lung cancer cell lines. In breast cancer tumor tissue, IGFR is overexpressed 6-14 fold and IGFR exhibits 2-4 fold higher kinase activity as compared to normal tissue (Webster, et al., *Cancer Res.* 56:2781 (1996); Pekonen, et al., *Cancer Res.* 48:1343 (1998)). Ninety percent of colorectal cancer tissue biopsies exhibit elevated IGFR levels wherein the extent of IGFR expression is correlated with the severity of the disease. Analysis of primary cervical cancer cell cultures and cervical cancer cell lines revealed 3-and 5-fold overexpression of IGFR, respectively, as compared to normal ectocervical cells (Steller, et al., *Cancer Res.* 56:1762 (1996)). Expression of IGFR in synovial sarcoma cells also correlated with an aggressive phenotype (i.e., metastasis and high rate of proliferation; Xie, et al., *Cancer Res.* 59:3588 (1999)).

By "overexpression" of the HER2, EGFR or IGFR receptor proteins is intended an abnormal level of expression of the HER2, EGFR, or IGFR proteins, respectively in a cell from a tumor within a specific tissue or organ of the patient relative to the level of expression in a normal cell from that tissue or organ. Patients having a cancer characterized by overexpression of the HER2, EGFR or IGFR receptors can be determined by standard assays known in the art. Overexpression can be measured in fixed cells of frozen or paraffin-embedded tissue sections using immununohistochemical (IHC) detection. When coupled with histological staining, localization of the targeted protein can be determined and extent of its expression within a tumor can be measured both qualitatively and semi-quantitatively. Such IHC detection assays are known in the art and include the Clinical Trial Assay (CTA), the commercially available LabCorp 4D5 test, and the commercially available DAKO HercepTest™ (DAKO, Carpinteria, Calif.). The latter assay uses a specific range of 0 to 3+ cell staining (0 being normal expression, 3+ indicating the strongest positive expression) to identify cancers having overexpression of the HER2 protein (see Trastuzumab full prescribing information; September 1998; Genentech, Inc., San Francisco, Calif.). Thus, patients having a cancer characterized by overexpression by immunohistochemistry (IHC) or Fluorescent in-situ hybridization (FISH) of the HER2 protein in the range of 1+, 2+, or 3+, particularly 2+ or 3+, more particularly 3+, would benefit from the methods of therapy of the present invention.

Using standard detection assays, several types of cancers have been characterized as having cells that overexpress the HER2, EGFR or IGFR receptors. Such cancers include, but are not limited to, breast, gastric, endometrial, salivary gland, nasopharyngeal, non-small cell lung, pancreatic, renal, ovarian, peritoneal, prostate, bladder, colorectal cancers, and glioblastomas. Methods of the invention are useful in the treatment/management of any such cancer whose cells overexpress C35 and either the HER2, EGFR or IGFR proteins. Of particular interest is breast cancer.

III. C35, HER2 and EGFR Antibodies

This invention relates to antibodies against C35, HER2 or EGFR (referred to herein as anti-C35, anti-HER2 or anti-EGFR antibodies; or C35, HER2 or EGFR antibodies) and methods of treating cancers using combinations of C35 and HER2 or C35 and EGFR antibodies. The description above regarding antibodies also applies to C35, HER2 and EGFR antibodies described herein.

The present invention encompasses antibodies (including molecules comprising, or alternatively consisting of, antibody fragments or variants thereof) that immunospecifically bind to a C35, HER2 or EGFR polypeptide or a fragment, variant, or fusion protein thereof. A C35 polypeptide includes, but is not limited to, the C35 polypeptide of SEQ ID NO:2. A HER2 polypeptide includes, but is not limited to, the HER2 polypeptide of Genbank Accession No. AAA75493 or AAA35978. An EGFR polypeptide includes, but is not limited to Genbank Accession Nos. AAB19486, AAH94761, AAI28420 and AAI18666. C35, HER2 or EGFR polypeptides may be produced through recombinant expression of nucleic acids. (See WO 01/74859 and U.S. Appl. No. 2004/0063907 for epitope-containing fragments of C35.)

The most widely recognized monoclonal antibody targeting HER2 receptor function is marketed under the tradename Herceptin® (commonly known as trastuzumab, huMAb4D5-8 or rhuMAb HER2; U.S. Pat. No. 5,821,337 and available from Genentech, Inc., San Francisco, Calif.). This recombinant humanized monoclonal antibody has high affinity for HER2. Early clinical trials with patients having extensive metastatic breast carcinomas demonstrate the ability of this monoclonal antibody to inhibit growth of breast cancer cells that overexpress HER2 (Baselga et al. (1996) J. Clin. Oncol. 14(3):737-744). In one such trial, monotherapy with trastuzumab in metastatic breast cancer patients yielded an overall response rate of 14% (2% complete responders and 12% partial responders). The median duration of response was 9.1 months, median survival was 12.8 months (ranging from 0.5 to 24+ months). Twenty-four percent of the patients were progression free at 5.8 months (Genentech, Inc., data on file). Degree of overexpression of HER2 was predictive of treatment effect.

While the most widely recognized HER2 antibody is trastuzumab, the methods of the invention are not limited to use of this antibody. Other HER2 antibodies of murine origin and their humanized and chimeric versions are also suitable for use in the methods of the present invention. Examples of other such HER2 antibodies include, but are not limited to, the 4D5 antibody (described in U.S. Pat. Nos. 5,677,171 and 5,772,997); and the 520C9 antibody and its functional equivalents, designated 452F2, 736G9, 741F8, 758G5, and 761B10 (described in U.S. Pat. No. 6,054,561); herein incorporated by reference. In addition, new HER2 antibodies can be generated using methods known in the art, or those described here.

Many studies have focused on the production of antibodies to the extracellular region of the EGFR. The mAbs generated mediate their anti-tumour activity primarily by blocking ligand binding and also the disruption of signaling. There were several mAbs initially developed by Peng et al. 1996 (Peng D et al Cancer Res 1996, 56:3666-3669) and Mendelson et al. 1997. (Mendelsohn J Clin Cancer Res 1997, 3:2703-2707) to specifically recognize the EGFR. Mabs 425, 528 IgG2a and 225 IgG1 were used to treat patients with head and neck squamous cell carcinoma (Sturgis E M, et al Otolaryngol. Head Neck Surg 1994, 111:633-643). Experimental work, including radiolabelling, has shown the mAb 425 to be an effective inhibitor of tumour growth including gliomas (Rodeck U et al J Cell Biochem 1987, 35:315-320; Brady L W et al Int J Radiat Oncol Biol Phys 1991, 22:225-230; Faillot T et al Neurosurgery 1996, 39:478-483). The IMC-C225 mAb specifically recognizes the EGFR, and has much potential in the treatment of cancers such as head and neck, colorectal, pancreas and lung. The mAb255 up-regulates p27 K1P1 and induces G1 arrest in a prostatic cancer cell line. IMC-C225, also known as Cetuximab (ERBITUX®) is a recombinant, human/mouse chimeric, monoclonal antibody that binds specifically to the extracellular domain of the human EGFR. Cetuximab is an EGFR antagonist, which blocks ligand binding to EGFR, prevents receptor activation, and inhibits growth of tumor cells that express EGFR. Cetuximab has been approved for use in combination with or without irinotecan in the treatment of patients with epidermal growth factor receptor-expressing, metastatic colorectal cancer who are refractory or can not tolerate irinotecan-based chemotherapy.

The mAb R3 was raised against the EGFR and was initially developed for use in radioimmunotherapy (Waterfield M D, et al. J. Cell Biochem. 1982, 20:149-161; Ramos-Suzarte M, et al. J. Nucl. Med. 1999, 40:768-775). Both chimeric and humanized forms of R3 have been produced and tested in African Green monkeys. The humanized version of R3 retained the same binding affinity of the mouse antibody, and was found to be 2-fold less immunogenic than the chimeric antibody. Preclinical studies of xenografts in mice using technetium-labeled mouse and humanized mAbs, showed a greater potential as a diagnostic tool with the humanized version than the murine. The rat anti-EGFR mAb, ICR62, effectively competes for ligand binding and eradicates human tumour xenografts (squamous cell carcinomas) in mice. Phase I clinical trials reported the antibody was administered safely to patients with squamous cell carcinomas, and it has since been used to investigate the signaling pathways of growth factor receptors and their ligands in head and neck squamous cell carcinoma cell lines (O-charoenrat P et al Clin. Exp. Metastasis 2000, 18:155-161; O-charoenrat P et al. Int. J. Cancer 2000, 86: 307-317; O-charoenrat P et al Oral Oncol. 2002, 38:627-640).

The present invention is further directed to antibody-based treatment methods which involve administering at least one C35 antibody and at least one HER2 antibody to a subject, preferably a mammal, and most preferably a human, for treating one or more cancers. The invention is also directed to antibody-based treatment methods which involve administering at least one C35 antibody and at least one EGFR antibody to a subject, preferably a mammal, and most preferably a human, for treating one or more cancers. Therapeutic compounds of the invention include, but are not limited to, antibodies of the invention (including fragments, analogs and derivatives thereof as described herein). The antibodies of the invention may be provided in pharmaceutically acceptable compositions as known in the art or as described herein.

Antibodies of the invention include, but are not limited to, polyclonal, monoclonal, multispecific, human, humanized or chimeric antibodies, single chain antibodies, scFvs, diabodies, triabodies, tetrabodies, minibodies, domain-deleted antibodies, Fab fragments, F(ab')2 fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Hybridoma cell lines 1F2.4.1 and 1B3.6.1, specific for C35 polypeptides, were previously prepared using hybridoma technology. Antibodies were isolated from hybridoma supernatants by protein G affinity purification using standard methods. Antibodies from two hybridoma cell lines, 1F2 and 1B3, specifically bind recombinant C35 protein in ELISA and Western Blot assays. Antibodies from hybridoma cell line 1F2 also specifically stain formalin fixed, paraffin embedded C35 positive tumors and cell lines by immunohistochemistry. Each of these antibodies is distinct, yet both are specific for C35 protein. It is possible to immunoprecipitate C35 protein from cell lysates with either of these antibodies and detect with the other. Competitive binding ELISA assays suggest that the monoclonal antibodies produced by hybridoma cell lines 1F2 and 1B3 bind different epitopes of the C35 protein.

Polynucleotides encoding the VL and VH regions of 1F2 and 1B3 antibodies were cloned into TOPO vectors as described Evans et al., U.S. Publication No. US20050158323, incorporated herein by reference, which were deposited with the American Type Culture Collection ("ATCC") on the date listed in Table 2, and given ATCC. Deposit Numbers listed in Table 2. The ATCC is located at 10801 University Boulevard, Manassas, Va. 20110-2209, USA. The ATCC deposits were made pursuant to the terms of the Budapest Treaty on the international recognition of the deposit of microorganisms for purposes of patent procedure.

Clone 1F2G, carrying the 1F2 heavy chain sequence, was deposited at the ATCC on Nov. 11, 2003 and given ATCC Deposit Number PTA-5639. Clone 1F2K, carrying the 1F2 light chain sequence, was deposited at the ATCC on Nov. 11, 2003 and given ATCC Deposit Number PTA-5640. Clone 1B3G, carrying the 1B3 heavy chain sequence, was deposited at the ATCC on Nov. 11, 2003 and given ATCC Deposit Number PTA-5637. Clone 1B3K, carrying the 1B3 light chain sequence, was deposited at the ATCC on Nov. 11, 2003 and given ATCC Deposit Number PTA-5638.

TABLE 1

Deposited Polynucleotide Clones Encoding Mouse Anti-C35 Variable Regions

| Polynucleotide Clone | ATCC Accession No. | Deposit Date |
|---|---|---|
| 1F2G | PTA-5639 | Nov. 11, 2003 |
| 1F2K | PTA-5640 | Nov. 11, 2003 |
| 1B3G | PTA-5637 | Nov. 11, 2003 |
| 1B3K | PTA-5638 | Nov. 11, 2003 |

The sequences of the mouse variable region genes and part of the vector of the deposited clones are set forth below.

```
1F2 murine anti-C35 Vgamma1 gene polynucleotide sequence (from clone 1F2G) (SEQ ID NO:3):

GAATTTAGCGGCCGCGAATTCGCCCTTcgactggagcacgggacactgacatggactgaaggagtagaaaa
catctctctcattagaggttgatctttgaggaaaacagggtgttgcctaaagg
ATGAAAGTGTTGAGTCTGTTGTACCTGTTGACAGCCATTCCTGGTATCCTGTCTGATGTACAGCTTCAGGA
GTCAGGACCTGGCCTCGTGAAACC
TTCTCAGTCTCTGTCTCTCACCTGCTCTGTCACTGGCTACTCCATCACCAGTGGTTATTTCTGGAACTGGA
TCCGG
                                     CDR1
CAGTTTCCAGGGAACAAACTGGAATGGATGGGCTACATAAGCTACGACGGTAGCAATAA
                           CDR2
CTCCAACCCATCTCTCAAAAATCGAATCTCCTTCACTCGTGACACATCTAAGAACCAGTTTTTCCTGAAGT
TTAATTCTGTGACTACTGACGACTCAGCTGCATATTACTGTACAAGAGGAACTACGGGGTTTGCTTACTGG
GGCCAAGGGACTCTGGTCACTGTCTCTGCAGCCAA
                                     CDR3
AACGACACCCCATCTGTCTATCCACTGGCCCCTGGATCTGCTGCCCAAACTAACTCCAAGGGCGAATTCG
TTTAAACCTGCAGGACTAGTCCCTT SIGNAL PEPTIDE = 18 AA
FR 1 = 30 AA
CDR 1 = 6 AA
FR 2 = 14 AA
CDR 2 = 16 AA
FR 3 = 32 AA
CDR 3 = 7 AA
FR 4 = 11 AA 1F2 VH amino acid sequence (encoded by clone 1F2G) (SEQ ID NO:4):

DVQLQESGPGLVKPSQSLSLTCVTGYSITSGYFWNWIRQFPGNKLEWMGYISYDGSNNSNPSLKNRISFT
RDTSKNQFFLKFNSVTTDDSAAYYCTRGTTGFAYWGQGTLVTVSA
```

1F2 murine anti-C35 kappa V gene polynucleotide sequence (from clone 1F2K) (SEQ ID NO:5):

*CGCGAATTCGCCCTT*cgactggagcacgaggacactgacatggactgaaggagtagaaaaattagctaggg
accaaaattcaaagacagaATGGATTTTCAGGTGCAGATTTTCAGCTTCCTGCTAATCAGTGCCTCAGTCA
GAATGTCCAGAGGA**CAAATTGTTCTCACCCAGTCTCCAGCAATCATGTCTGCATCTCCAGGGGAGAAGGTC
ACCATATCCTGC**AGTGCCAGCTCAAGTGTAAGTTACATG
              CDR1
AACTGGTACCAGCAGAAGCCAGGATCCTCCCCCAAACCCTGGA
TTTATCACACATCCAACCTGGCTTCTGGAGTCCCTGCTCGCTTCAGTGGCAGTGGGTCT
              CDR2
GGGACCTCTTACTCTCTCACAATCAGCAGCATGGAGGCTGAAGATGCTGCCACTTATTACTGC
CAACAGTATCATAGTTACCCACCCACGTTCGGAGGGGGGACCAAGCTGGAAATAA
              CDR3
AA*CGGGCTGATGCTGCACCAACTGTATCCATCTTCCCACCATCCAGTGAGCAAAGGGCGAATTCGTTT*

SIGNAL PEPTIDE = 22 AA
FR1 = 23 AA
CDR 1 = 10 AA
FR 2 = 15 AA
CDR 2 = 7 AA
FR 3 = 32 AA
CDR 3 = 9 AA
FR 4 = 10 AA

1F2-VK amino acid sequence (encoded by clone 1F2K) (SEQ ID NO:6):

QIVLTQSPAIMSASPGEKVTISCSASSSVSYMNWYQQKPGSSPKPWIYHTSNLASGBPARFSGSGSGTSYS
LTISSMEAEDAATYYCQQYHSYPPTFGGGTKLEIK

1B3 murine anti-C35 Vgamma V-gene (encoded by clone 1B3G) (NC1-A7 V139-D-J1
(VH36-60) M13281)(SEQ ID NO:7):

*CGCGAATTCGCCCTT*cgactggagcacgaggacactggacatggactgaaggagtagaaaatctctctcac
tgaggctgattttgaagaaaggggttgtagcctaaaagATGATGGTGTTAAGTCTTCTGTACCTGTTGA
CAGCCCTTCCGGGTATCCTGTCA**GAGGTGCAGCTTCAGGAGTCAGGACCTAGCCTCGTGAAACCTTCTCAG
ACTCTGTCCCTCACCTGTTCTGTCACTGGCGACTCCATCACCAGTGGTTACTGGAACTGGATCCGGAAATT
CCCAGGAAATA**
              CDR1
AACTTGAATACGTGGGGTACATAAGCTACAGTGGTGGCACTTACTACAATCCATCTCTC
              CDR2
**AAAAGTCGAATCTCCATCACTCGAGACACATCCAAGAACCACTACTACCTGCAGTTGAATTCTGTGACTAC
TGAGGACACAGCCACATATTACTGTGCAAGA**GGTGCTTACTACGGGGGGGCCTTTTTTCCTTACTTCGATG
TCTGGGGCGCTGGGACCACGGTCACCGTCTCCTCA
              CDR3
GCCAAAACGACACCCCCATCTGTCTATCCACTGGCCCCTGGATCTGCTGCCCAAACTAACTCCAA*GGGCGA
ATTC*GTTTAAACCTGC SIG PEP = 18 AA
FR1 = 30 AA
CDR 1 = 5 AA
FR2 = 14 AA
CDR2 = 16 AA
FR 3 = 32 AA
CDR 3 = 14 AA
FR 4 = 11 AA 1B3 VH amino acid sequence (encoded by clone 1B3G) (SEQ ID NO:8):

EVQLQESGPSLVKPSQTLSLTCSVTGDSITSGYWNWIRKFPGNKLEYVGYISYSGGTYYNPSLKSRISITR
DTSKNHYYLQLNSVTTEDTATYYCARGAYYGGAFFPYFDVWGAGTTVTSS

1B3 murine anti-C35 kappa V-gene (from clone 1B3K) (SEQ ID NO:9):

*GAATTCGCCCTT*cccctggagcacga
ggacactgacatggactgaaggagtagaaaatcagttcctgccaggacacagtttagatATGAGGTTCCAG
GTTCAGGTTCTGGGGCTCCTTCTGCTCTGGATATCAGGTGCCCACTGT**GATGTCCAGATAACCCAGTCTCC
ATCTTTTCTTGCTGCATCTCCTGGAGAAACCATTACTATTAATTGC**AGGGCAAGTAAGTACATTAGCA
              CDR1
AACATTTAGTCTGGTATCAGGAGAAACCTGGAGAAACTAAAAAGCTTCTTATCTACTCTGGATCCACTTTG
CAATCTGGACTTCCATCAAGGTTCAGTGGCAGTGGATCTGGTACAGA
CDR2
TTTCACTCTCACCATCAGTAGCCTGGAGCCTGAAGATTTTGCAATGTATTACTGTCAACAGCATAATGAAT
ACCCGCTCACGTTCGGTGCTGGGACCAAGCTGGAGCTGAAACGGGCT
CDR3
GATGCTGCACCAACTGTATCCATCTTCCCACCATCCAGTGAGCAAA*GGGCGAATTC*

```
SP  = 20 AA
FR1 = 23 aa
CDR1 = 11 aa
FR2 = 15 aa
CDR2 = 7 AA
FR3 = 32 aa
CDR 3 = 9 AA
FR 4 = 10 AA

1B3 VK amino acid sequence (encoded by clone 1B3K) (SEQ ID NO:10):

DVQITQSPSFLAASPGETITINCRASKYISKHLVWYQEKPGETKKLLIYSGSTLQSGLPSRFSGSGSGTDF

TLTISSLEPEDFAMYYCQQHNEYPLTFGAGTKLEK
```

Italics = Topo vector sequence (included in deposited clone)
dotted underline = EcoR1 cloning site of Topo vector
Lowercase = 5′ untranslated region including generacer primer
ATG = Murine signal peptide begin
bold = Frame work regions (FWR)
double underline = CDR1, CDR2, CDR3
underline = 5′ portion of mouse IgG1 or kappa constant region C35 antibodies of the invention include antibodies which immunospecifically bind a C35 polypeptide, polypeptide fragment, or variant of SEQ ID NO:2, and/or an epitope, of the present invention (as determined by immunoassays well known in the art for assaying specific antibody-antigen binding).

As used herein the term "isolated" is meant to describe a compound of interest (e.g., a C35 antibody) that is in an environment different from that in which the compound naturally occurs. "Isolated" is meant to include compounds that are within samples that are substantially enriched for the compound of interest and/or in which the compound of interest is partially or substantially purified.

As used herein, the terms "substantially enriched" and "substantially purified" refers to a compound that is removed from its natural environment and is at least 60% free, preferably 75% free, and most preferably 90% free from other components with which it is naturally associated. As used here, an antibody having the "same specificity" as a reference antibody means the antibody binds the same epitope as the reference antibody. The determination of whether an antibody binds the same epitope as a reference antibody may be performed using the assays described herein below.

The antibodies derived from mouse hybridoma cell lines discussed herein (1F2, 1B3, MAbc0009, MAb 163, MAb 165, MAb 171) are described in copending U.S. application Ser. No. 11/812,996. Polynucleotides encoding the VL and VH regions of these antibodies were deposited with the American Type Culture Collection ("ATCC") on Nov. 11, 2003. Clone IF2G was deposited at the ATCC on Nov. 11, 2003 and given ATCC Deposit Number PTA-5639. Clone 1F2K was deposited at the ATCC on Nov. 11, 2003 and given ATCC Deposit Number PTA-5640. Clone 1B3G was deposited at the ATCC on Nov. 11, 2003 and given ATCC Deposit Number PTA-5637. Clone 1B3K was deposited at the ATCC on Nov. 11, 2003 and given ATCC Deposit Number PTA-5638.

Use of 1F2, 1B3, MAbc0009, MAb 163, MAb 165, or MAb 171 antibodies are for illustrative purposes and the methods are not to be construed as limited to these antibodies. Any C35 antibodies, including but not limited to those listed in copending U.S. application Ser. No. 11/812,996, are useful in the methods of the present invention Preferably, analogs of exemplified antibodies differ from exemplified antibodies by conservative amino acid substitutions. For purposes of classifying amino acids substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Most preferably the antibodies are human, chimeric (e.g., human mouse chimeric), or humanized antibodies or antigen-binding antibody fragments of the present invention, including, but not limited to, Fab, Fab' and F(ab')2, Fd, single-chain Fvs (scFv), diabodies, triabodies, tetrabodies, minibodies, single-chain antibodies, disulfide-linked Fvs (sdFv), and intrabodies, and fragments comprising either a VL or VH region. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Preferred antibodies in the therapeutic methods of the invention are those containing a deletion of the CH2 domain.

Antibodies for use with the methods of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, or by size in contiguous amino acid residues. Antibodies which specifically bind any epitope or polypeptide of the present invention may also be excluded. Therefore, the present invention includes antibodies that specifically bind polypeptides of the present invention, and allows for the exclusion of the same.

Antibodies for use with the methods of the present invention may also be described or specified in terms of their binding affinity to a polypeptide of the invention. Preferred binding affinities include those with a dissociation constant or Kd less than $5 \times 10(-7)$ M, $10(-7)$ M, $5 \times 10(-8)$ M, $10(-8)$ M, $5 \times 10(-9)$ M, $10(-9)$ M, $5 \times 10(-10)$ M, $10(-10)$ M, $5 \times 10(-11)$ M, $10(-11)$ M, $5 \times 10(-12)$ M, $10(-12)$ M, $5 \times 10(-13)$ M, $10(-13)$ M, $5 \times 10(-14)$ M, $10(-14)$ M, $5 \times 10(-15)$ M, or $10(-15)$ M.

Certain antibodies for use with the methods of the invention have an affinity for C35 the same as or similar to the affinity of the antibodies 1F2, 1B3, MAbc0009, MAb 163, MAb 165 and MAb 171. Preferably, the antibodies of the invention have an affinity for C35 that is higher than the affinity of the antibodies 1F2, 1B3, MAbc0009, MAb 163, MAb 165 and MAb 171.

The invention also encompasses the use of antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to C35, HER2, EGFR, and/or IGFR polypeptide; the ability to substantially inhibit or abolish C35, HER2, EGFR and/or IGFR polypeptide mediated biological activity; the ability to kill C35, HER2, EGFR and/or IGFR-associated cancer cells; or the ability to induce apoptosis of cancer cells expressing HER2, EGFR and/or IGFR. Optionally, the antibodies of the invention will bind to the same epitope as at least one of the antibodies specifically referred to herein. Such epitope binding can be routinely determined using assays known in the art and described herein below.

Humanized immunoglobulins and human antibody variants of the invention have variable framework regions substantially from a human immunoglobulin (termed an acceptor immunoglobulin), and CDRs substantially from the mouse C35, HER2, EGFR and/or EGFR VH and VL regions (referred to as the donor immunoglobulin). The constant region(s), if present, are also substantially from a human immunoglobulin. The humanized antibodies and human antibody variants exhibit a specific binding affinity for C35, HER2, EGFR or IGFR of at least $10(2), 10(3), 10(4), 10(5), 10(6), 10(7), 10(8), 10(9),$ or $10(10) M(-1)$. Usually the upper limit of binding affinity of the humanized antibodies and human antibody variants for human C35, HER2 or EGFR is within a factor of 3, 4, 5 or 10 of that of the mouse antibodies 1F2 or 1B3. Often the lower limit of binding affinity for C35 is also within a factor of 3, 4, 5 or 10 of that of the mouse antibodies in 1F2 or 1B3. Preferred anti-C35 humanized immunoglobulins and human antibody variants compete with the mouse antibodies 1F2 or 1B3 for binding to C35 and prevent C35 from binding to the respective mouse or human antibody.

The heavy and light chain variable regions of possible human acceptor antibodies are described by Kabat, Sequences of Proteins of Immunological Interest (National Institutes of Health, Bethesda, Md., 1987 and 1991). The human acceptor antibody is chosen such that its variable regions exhibit a high degree of sequence identity with those of the mouse C35 or HER2 antibody. The heavy and light chain variable framework regions can be derived from the same or different human antibody sequences. The human antibody sequences can be the sequences of naturally occurring human antibodies or can be consensus sequences of several human antibodies.

The design of humanized immunoglobulins can be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulins at that position, whereas the corresponding amino acid in the donor immunoglobulin is typical for human immunoglobulins in that position;

(b) the position of the amino acid is immediately adjacent to one of the CDRs; or (c) the amino acid is capable of interacting with the CDRs (see, Queen et al., WO 92/11018., and Co et al., *Proc. Natl. Acad. Sci. USA* 88, 2869 (1991), respectively, both of which are incorporated herein by reference). For a detailed description of the production of humanized immunoglobulins see, Queen et al. and Co et al.

Usually the CDR regions in humanized antibodies and human antibody variants are substantially identical, and more usually, identical to the corresponding CDR regions in the mouse or human antibody from which they were derived. It is possible to make one or more amino acid substitutions of CDR residues without appreciably affecting the binding affinity of the resulting humanized immunoglobulin or human antibody variant and, occasionally, substitutions of or within CDR regions can enhance binding affinity. See, e.g., Iwahashi et al., *Mol. Immunol.* 36: 1079-1091 (1999); Glaser et al., *J. Immunol.* 149(8): 2607-2614 (1992); and Tamura et al., *J. Immunol.* 164: 1432-1441 (2000).

Other than for the specific amino acid substitutions discussed above, the framework regions of humanized immunoglobulins and human antibody variants are usually substantially identical, and more usually, identical to the framework regions of the human antibodies from which they were derived (acceptor immunoglobulin). Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin or human antibody variants.

Phage-display technology offers powerful techniques for selecting analogs that have substantial sequence identity to a parent sequence, while retaining binding affinity and specificity (see, e.g., Dower et al., WO 91/17271; McCafferty et al., WO 92/01047; and Huse, WO 92/06204; US 2002/0123057A1; each of which is herein incorporated by reference).

The variable segments of humanized antibodies or human antibody variants produced as described supra are typically linked to at least a portion of an immunoglobulin constant region (Fc), typically that of a human immunoglobulin. Human constant region DNA sequences can be isolated in accordance with well-known procedures from a variety of human cells, such as immortalized B-cells (see Kabat et al., supra, and WO 87/02671). The antibody may contain both light chain and heavy chain constant regions. The heavy chain constant region may include CH1, hinge, CH2, CH3, and, sometimes, CH4 regions. For therapeutic purposes, the CH2 domain may be deleted or omitted.

The humanized antibody or human antibody variants include antibodies having all types of constant regions, including IgM, IgG, IgD, IgA and IgE, and any isotype, including IgG1, IgG2, IgG3 and IgG4. When it is desired that the humanized antibody or human antibody variants exhibit cytotoxic activity, the constant domain is usually a complement-fixing constant domain and the class is typically IgG1. When such cytotoxic activity is not desirable, the constant domain can be of the IgG2 class. The humanized antibody or human antibody variants may comprise sequences from more than one class or isotype.

Chimeric antibodies are also encompassed for use in the present invention. Such antibodies may comprise a VH region and/or VL region fused to the CH region and/or CL region of another species, such as human or mouse or horse, etc. In preferred embodiments, a chimeric antibody comprises the VH and/or VL region encoded by a murine anti-C35 or anti-HER2 antibody fused to human C regions. The human CH2 domain may be deleted when antibodies are used in therapeutic purposes. Chimeric antibodies encompass antibody fragments, as described above.

The variable segments of chimeric antibodies produced as described supra are typically linked to at least a portion of an immunoglobulin constant region (Fc), typically that of a human immunoglobulin. Human constant region DNA sequences can be isolated in accordance with well-known procedures from a variety of human cells, such as immortalized B-cells (see Kabat et al., supra, and WO 87/02671). The antibody may contain both light chain and heavy chain constant regions. The heavy chain constant region may include CH1, hinge, CH2, CH3, and, sometimes, CH4 regions. For therapeutic purposes, the CH2 domain may be deleted or omitted.

Chimeric antibodies include antibodies having all types of constant regions, including IgM, IgG, IgD, IgA and IgE, and any isotype, including IgG1, IgG2, IgG3 and IgG4. When it is desired that the chimeric antibody exhibit cytotoxic activity, the constant domain is usually a complement-fixing constant domain and the class is typically IgG1. When such cytotoxic activity is not desirable, the constant domain can be of the IgG2 class. The chimeric antibody may comprise sequences from more than one class or isotype.

A variety of methods are available for producing such immunoglobulins. Because of the degeneracy of the genetic code, a variety of nucleic acid sequences encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

Once expressed, the whole antibodies, their dimers, individual light and heavy chains, or other immunoglobulin forms of the present invention can be purified according to standard procedures in the art, including ammonium sulfate precipitation, affinity columns, column chromatography, gel electrophoresis and the like (see, generally, Scopes, R., Protein Purification, Springer-Verlag, N.Y. (1982), which is incorporated herein by reference). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally), in developing and performing assay procedures, immunofluorescent stainings, and the like. (See, generally, *Immunological Methods*, Vols. I and II, Lefkovits and Pernis, eds., Academic Press, New York, N.Y. (1979 and 1981), or detect C35 or diagnose a C35-associated cancer.

As discussed in more detail below, the antibodies for use in the methods of the present invention may be used either alone, in combination with each other, or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387, which are herein incorporated by reference in their entireties.

The antibodies for use in the methods of the invention include derivatives that are modified, i.e., by the covalent attachment of any type of molecule to the antibody such that covalent attachment does not prevent the antibody from binding C35, HER2, EGFR, or IGFR. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Antibodies for use in the methods of the invention can be composed of amino acids joined to each other by peptide bonds or modified peptide bonds, i.e., peptide isosteres, and may contain amino acids other than the 20 gene-encoded amino acids. The antibodies for use in the methods of the invention may be modified by natural processes, such as posttranslational processing, or by chemical modification techniques which are well known in the art. Such modifications are well described in basic texts and in more detailed monographs, as well as in a voluminous research literature. Modifications can occur anywhere in the antibodies, including the peptide backbone, the amino acid side-chains and the amino or carboxyl termini. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

A further embodiment of the invention relates to a polypeptide which comprises the amino acid sequence of an antibody sequence having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises an antibody sequence, which contains at least one, but not more than 10, 9, 8, 7, 6, 5, 4, 3, 2 or 1 amino acid substitutions. In specific embodiments, the number of additions, substitutions, and/or deletions in the antibody sequence is 1-5, 5-10, 5-25, 5-50, 10-50 or 50-150. For substitutions, conservative amino acid substitutions are preferable. The substitutions may be within the framework regions or the CDRs or both.

The description in this section applies to C35, HER2, EGFR and/or IGFR antibodies useful in the method of the invention. Such antibodies may be conjugated to or complexed with a toxin; as described herein, or may be unconjugated or uncomplexed.

IV. C35, HER2 and EGFR Antibody Polypeptides

The present invention is further directed to isolated polypeptides which make up the antibodies of the invention, and polynucleotides encoding such polypeptides. The antibodies of the present invention comprise polypeptides, e.g., amino acid sequences encoding C35-, HER2- or EGFR-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the present invention provides an isolated polypeptide comprising, consisting essentially of, or consisting of an immunoglobulin heavy chain variable region (VH), where at least one of CDRs of the heavy chain variable region or at least two of the CDRs of the heavy chain variable region are at least 80%, 85%, 90% 95%, 99%, or 100% identical to reference heavy chain CDR1, CDR2 or CDR3 amino acid sequences from the C35, HER2 or EGFR antibodies referenced above. Alternatively, the CDR1, CDR2 and CDR3 regions of the VH are at least 80%, 85%, 90%, 95%, 99% or 100% identical to reference heavy chain CDR1, CDR2 and CDR3 amino acid sequences from the antibodies referenced above.

In certain embodiments, an antibody or antigen-binding fragment thereof comprising, consisting essentially of, or consisting of a one or more of the VH polypeptides described above specifically or preferentially binds to the same epitope as a monoclonal antibody selected from the group consisting of 1F2, 1B3, MAbc0009, MAb 163, MAb 165 and MAb 171, or will competitively inhibit such a monoclonal antibody from binding to C35.

In certain embodiments, an antibody or antigen-binding fragment thereof comprising, consisting essentially of, or consisting of one or more of the VH polypeptides described above specifically or preferentially binds to a C35, HER2 or EGFR polypeptide or fragment thereof, or a C35, HER2 or EGFR variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polypeptide comprising, consisting essentially of, or consisting of an immunoglobulin light chain variable region (VL), where at least one of the CDRs of the light chain variable region or at least two of the CDRs of the light chain variable region are at least 80%, 85%, 90%, 95%, 99% or 100% identical to reference heavy chain CDR1, CDR2, or CDR3 amino acid sequences from C35, HER2 or EGFR antibodies referenced above. Alternatively, the CDR1, CDR2 and CDR3 regions of the VL are at least 80%, 85%, 90%, 95%, 99% or 100% identical to reference light chain CDR1, CDR2, and CDR3 amino acid sequences from the antibodies referenced above.

In certain embodiments, an antibody or antigen-binding fragment thereof comprising, consisting essentially of, one or more of the VL polypeptides described above specifically or preferentially binds to the same epitope as a monoclonal antibody selected from the group consisting of 1F2, 1B3, MAbc0009, MAb 163, MAb 165 and MAb 171, or will competitively inhibit such a monoclonal antibody from binding to C35.

In certain embodiments, an antibody or antigen-binding fragment thereof comprising, consisting essentially of, or consisting of a one or more of the VL polypeptides described above specifically or preferentially binds to a C35, HER2 or EGFR polypeptide or fragment thereof, or a C35, HER2 or EGFR variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

It will also be understood by one of ordinary skill in the art that C35, HER2 or EGFR antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, or 99% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain antibody polypeptides of the invention comprise, consist essentially of, or consist of an amino acid sequence derived from a human amino acid sequence. However, certain antibody polypeptides comprise one or more contiguous amino acids derived from another mammalian species. For example, an antibody of the present invention may include a primate heavy chain portion, hinge portion, or antigen binding region. In another example, one or more murine-derived amino acids may be present in a non-murine antibody polypeptide, e.g., in an antigen binding site of a C35, HER2 or EGFR antibody. In certain therapeutic applications, C35-, HER2- or EGFR-specific antibodies, or antigen-binding fragments, variants, or analogs thereof are designed so as to not be immunogenic in the animal to which the antibody is administered.

In certain embodiments, an antibody polypeptide of the invention comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

An antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into C35 or HER2 antibodies for use in the treatment methods disclosed herein.

V. Fusion Proteins and Antibody Conjugates

C35, HER2, EGFR or IGFR antibodies, or antigen-binding fragments, variants, or derivatives thereof for use in the methods of the invention may further be recombinantly fused to a heterologous polypeptide at the N- or C-terminus or chemically conjugated (including covalent and non-covalent conjugations) to polypeptides or other compositions. For example, the antibodies of the invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

C35, HER2, EGFR or IGFR antibodies, or antigen-binding fragments, variants, or derivatives thereof of the invention include derivatives that are modified, i.e., by the covalent attachment of any type of molecule to the antibody such that covalent attachment does not prevent the antibody binding C35, HER2, EGFR or IGFR, respectively. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

C35, HER2, EGFR or IGFR antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. The antibodies of the invention may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising a C35, HER2, EGFR or IGFR antibody, or antigen-binding fragment, variant, or derivative thereof, and a heterologous polypeptide. The heterologous polypeptide to which the antibody is fused may be useful for function or is useful to target the C35, HER2, EGFR or IGFR expressing cells. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$ CDRs of a C35-, HER2-, EGFR- or IGFR-specific antibody, or fragments, variants, or derivatives thereof, or the amino acid sequence of any one, two, three of the $V_L$ CDRs of a C35-, HER2-, EGFR- or IGFR-specific antibody, or fragments, variants, or derivatives thereof, and a heterologous polypeptide sequence. In one embodiment, the fusion protein comprises a polypeptide having the amino acid sequence of a $V_H$ CDR3 of a C35-specific antibody of the present invention, or fragment, derivative, or variant thereof, and a heterologous polypeptide sequence, which fusion protein specifically binds to at least one epitope of C35. In another embodiment, a fusion protein comprises a polypeptide having the amino acid sequence of at least one $V_H$ region of a C35-specific antibody of the invention and the amino acid sequence of at least one $V_L$ region of a C35-specific antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds at least one epitope of C35. In yet another embodiment, a fusion protein for use in the diagnostic and treatment methods disclosed herein comprises a polypeptide having the amino acid sequence of any one, two, three or more of the $V_H$ CDRs of a C35-specific antibody and the amino acid sequence of any one, two, three or more of the $V_L$ CDRs of a C35-specific antibody, or fragments or variants thereof, and a heterologous polypeptide sequence. Preferably, two, three, four, five, six, or more of the $V_H$CDR(s) or $V_L$CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349: 164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol. Vol.* 115, Abstract No. 1448 (1991)).

As discussed elsewhere herein, C35, HER2, EGFR, or IGFR antibodies, or antigen-binding fragments, variants, or derivatives thereof for use in the methods of the invention may be fused to heterologous polypeptides to increase the in vivo half life of the polypeptides. For example, in one embodiment, PEG can be conjugated to the antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Antibodies for use in the methods of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof for use in the methods of the invention can be labeled or conjugated either before or after purification, when purification is performed.

In particular, C35, HER2, EGFR or IGFR antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

The present invention further encompasses antibodies, or antigen-binding fragments, variants, or derivatives thereof for use in the methods of the invention conjugated to a diagnostic or therapeutic agent. The antibodies can be used diagnostically to, for example, monitor the development or progression of a disease as part of a clinical testing procedure to, for example, determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

VI. Expression of Antibody Polypeptides

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide C35, HER2, EGFR or IGFR antibodies, or antigen-binding fragments, variants, or derivatives thereof of the invention, the polynucleotides encoding the antibodies are typically inserted in an expression vector for introduction into host cells that may be used to produce the desired quantity of an antibody of the invention.

Recombinant expression of an antibody of the invention, or fragment, derivative or analog thereof, e.g., a heavy or light chain of an antibody which binds to a target molecule described herein requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

More generally, once the vector or DNA sequence encoding a monomeric subunit of the C35, HER2, EGFR or IGFR antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody or fragment thereof of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus are an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding C35, HER2, EGFR, or IGFR antibodies, or antigen-binding fragments, variants, or derivatives thereof for use in the methods of the invention can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule for use in the methods of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002/0123057 A1.

VII. Treatment Methods Using Combination Therapies Comprising Anti-C35 Antibodies The present invention is directed to using combinations of antibodies of the invention to treat hyperproliferative diseases, for example, to treat cancer. In some embodiments, at least one anti-C35 antibody and at least one anti-HER2 antibody are administered. In a specific embodiment, one anti-C35 antibody one anti-HER2 antibody are administered. In a more specific embodiment, the anti-C35 antibody is 1B3 or 1F2 or a variant or derivative thereof. In another embodiment, the anti-HER2 antibody is trastuzumab. In other embodiments, at least one anti-C35 antibody and at least one anti-EGFR antibody may be administered. In a specific embodiment, one anti-C35 antibody one anti-EGFR antibody are administered. In a more specific embodiment, the anti-C35 antibody is 1B3 or 1F2 or a variant or derivative thereof. In another embodiment, the anti-EGFR antibody is cetuximab. In a specific embodiment, the cancer is breast cancer. In a more specific embodiment, the breast cancer is an intraductal carcinoma.

In other embodiments, two or more anti-C35 antibodies and/or two or more anti-HER2 and/or two or more anti-EGFR antibodies are administered. In other embodiments, one or more anti-IGFR antibodies are administered in combination with one or more anti-C35 antibodies. Further, in additional embodiments, any of the aforementioned antibody combinations is administered with a therapeutic agent. In a particular embodiment, the therapeutic agent is a chemotherapeutic agent. In a more particular embodiment, the chemotherapeutic agent is paclitaxel. In another particular embodiment, the chemotherapeutic agent is adriamycin. In another particular embodiment, the chemotherapeutic agent is cisplatin. In a further embodiment, the therapeutic agent is radiation. In a specific embodiment, the cancer is breast cancer. In a more specific embodiment, the breast cancer is an intraductal carcinoma.

In embodiments where at least two antibodies directed to a particular polypeptide are administered (e.g., two anti-C35, two anti-HER2 two anti-EGFR and/or two anti-IGFR antibodies), the antibodies can each bind to different epitopes within the polypeptide. For example, for C35, one antibody can bind to an epitope located within residues 105-115 of C35 (SEQ ID NO:2) while the other can bind an epitope located within resides 48-104 of C35 (SEQ ID NO:2). In a particular embodiment, the C35 antibodies that bind eptiopes within these regions of C35 are 1B3 and 1F2, or variants or derivatives thereof (e.g. humanized 1B3 and/or humanized 1 F2)

The present invention also includes administering two antibodies that bind the same epitope. For example, two different C35 antibodies that bind to an epitope located within residues 105-115 of C35 (SEQ ID NO:2) can be administered. Similarly, two different C35 antibodies that bind to an epitope located within residues 48-104 of C35 (SEQ ID NO:2) can be administered.

In some embodiments, the antibodies for use in the methods of the present invention can be selected based on their ability to bind to a C35, HER2 or EGFR polypeptide or fragment thereof, or a C35, HER2 or EGFR variant polypeptide, with an affinity characterized by a dissociation constant ($K_D$) which is less than the $K_D$ of a reference monoclonal antibody. The present invention includes all C35, HER2 or EGFR antibodies disclosed herein as reference monoclonal antibodies for the purposes of these embodiments. In a particular embodiment, monoclonal antibodies 1B3 and 1F2, as disclosed herein and in U.S. Appl. Publ. Nos. 2005/0158323A1 and 20040063907A1 (incorporated herein by reference in their entireties), are the reference antibodies. In another embodiment, the reference monoclonal antibody is MAb 163, as disclosed in copending U.S. application Ser. No. 11/812,996 (incorporated herein by reference in its entirety). Accordingly, in some embodiments, the C35 antibody or antibodies bind to a C35 polypeptide or fragment thereof, or a C35 variant polypeptide, with an affinity characterized by a dissociation constant ($K_D$) which is less than the $K_D$ of MAb 1B3, MAb 1F2, or MAb 163. Also, in some embodiments, the anti-C35 antibodies for use in the present invention bind to the same epitopes as the reference antibodies, in particular those anti-C35 antibodies disclosed in U.S. Appl. Publ. Nos. 2005/0158323A1 and 20040063907A1 and U.S. application Ser. No. 11/812,996 (e.g., MAb 1B3, MAb 1F2, or MAb 163.

In another particular embodiment, the anti-EGFR antibody, cetuximab, is the reference antibody. Accordingly, in some embodiments, the anti-EGFR antibody or antibodies bind to an EGFR polypeptide or fragment thereof, or an EGFR variant polypeptide, with an affinity characterized by a dissociation constant ($K_D$) which is less than the $K_D$ of cetuximab. In another particular embodiment, the anti-HER2 antibody, trastuzumab, is the reference antibody. Accordingly, in some embodiments, the anti-HER2 antibody or antibodies bind to a HER2 polypeptide or fragment thereof, or a HER2 variant polypeptide, with an affinity characterized by a dissociation constant ($K_D$) which is less than the $K_D$ of trastuzumab.

In other embodiments, the antibodies for use in the methods of the present invention can be selected based on their ability to bind to an IGFR polypeptide or fragment thereof, or an IGFR variant polypeptide, with an affinity characterized by a dissociation constant ($K_D$) which is less than the $K_D$ of a reference monoclonal antibody that specifically binds to IGFR. Examples of IGFR antibodies include HU, 15H12, 19D12, 15H12/19D12 LCA, 15H12/19D12 LCB, 15H12/19D12 LCC, 15H12/19D12 LCD, 15H12/19D12 LCE, 15H12/19D12 LCF, 15H12/19D12 HCA or 15H12/19D12 HCB as described in U.S. Pat. No. 7,217,796; α-IR3 (Kull et al., *J. Biol. Chem.* 258:6561 (1983)); 1H7 (Li et al., *Biochem. Biophys. Res. Comm.* 196:92-98 (1993), Santa Cruz biotechnology, Inc. Santa Cruz, Calif.) and MAB391 (R&D Systems; Minneapolis, Minn.).

In some embodiments, the present invention includes administering one anti-C35 antibody and one anti-HER2 antibody with or without an additional therapeutic agent for treating a hyperproliferative disease, e.g., cancer. Any antibody that specifically binds to C35 or HER2, including but not limited to those disclosed herein, may be used in this method. In some embodiments, the antibodies are administered before, after, or concurrently with the administration of the therapeutic agent. In one embodiment, MAb 1F2 or 1B3 is administered with trastuzumab and a therapeutic agent. In one embodiment, the therapeutic agent is a chemotherapeutic agent selected from the group consisting of paclitaxel, adriamycin, and cisplatin. In a specific embodiment, the cancer is breast cancer. In a more specific embodiment, the breast cancer is an intraductal carcinoma.

In some embodiments, the present invention includes administering one anti-C35 antibody and one anti-EGFR antibody with or without an additional therapeutic agent for treating a hyperproliferative disease, e.g., cancer. Any antibody that specifically binds to C35 or EGFR, including but not limited to those disclosed herein, may be used in this method. In some embodiments, the antibodies are administered before, after, or concurrently with the administration of the therapeutic agent. In one embodiment, MAb 1F2 or 1B3 is administered with cetuximab and a therapeutic agent. In one embodiment, the therapeutic agent is a chemotherapeutic agent selected from the group consisting of paclitaxel, adriamycin, and cisplatin. In a specific embodiment, the cancer is breast cancer. In a more specific embodiment, the breast cancer is an intraductal carcinoma.

In some embodiments, the present invention includes administering one anti-C35 antibody and one anti-IGFR antibody with or without an additional therapeutic agent for treating a hyperproliferative disease, e.g., cancer. Any antibody that specifically binds to C35 or IGFR, including but not limited to those disclosed herein, may be used in this method. In some embodiments, the antibodies are administered before, after, or concurrently with the administration of the therapeutic agent. In one embodiment, MAb 1F2 or 1B3 is administered with cetuximab and a therapeutic agent. In one embodiment, the therapeutic agent is a chemotherapeutic agent selected from the group consisting of paclitaxel, adriamycin, and cisplatin. In a specific embodiment, the cancer is breast cancer. In a more specific embodiment, the breast cancer is an intraductal carcinoma.

In some embodiments, the above-described C35/HER2 or C35/EGFR combination therapies are administered with an IGFR antibody. The C35/HER2/IGFR or C35/EGFR/IGFR antibody compositions can be administered with or without administration of a therapeutic agent.

In some embodiments, the present invention includes administering at least two C35 antibodies and one HER2 antibody with a therapeutic agent. In other embodiments, at least two C35 antibodies and at least two HER2 antibodies are administered with a therapeutic agent. Any combination of C35 and HER2 antibodies may be administered and all combinations are included in the present invention. In some preferred embodiments, the present invention includes administering at least two C35 antibodies and one EGFR antibody with a therapeutic agent. In other embodiments, at least two C35 antibodies and at least two EGFR antibodies are administered with a therapeutic agent. Any combination of C35 and EGFR antibodies may be administered and all combinations are included in the present invention. Also encompassed in the present invention are administration of variants (e.g. humanized versions, affinity optimized versions) or derivatives of any of these antibodies in combination with each other and therapeutic agents (e.g., a chemotherapeutic agent). Also encompassed in the present invention are compositions comprising combinations of antibodies with or without therapeutic agents.

In embodiments where the subject with cancer is a human, the antibodies administered are preferably fully human or humanized. These humanized antibodies can include a humanized form of any antibody disclosed herein, for example, humanized versions of 1F2 and/or 1B3. Also encompassed within the present invention are affinity optimized versions of the antibodies, including, but not limited to 1B3 and 1F2.

The methods and compositions of the invention can be used to treat hyperproliferative diseases, disorders, and/or conditions, including neoplasms. Examples of hyperproliferative diseases, disorders, and/or conditions that can be treated by the method of the invention include, but are not limited to neoplasms located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Other examples of such hyperproliferative disorders include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal, Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In some particular embodiments, the hyperproliferative disorder is a cancer of a tissue or organ selected from the group consisting of breast, bladder, liver, colon, ovary and skin. In a specific embodiment, the cancer is breast cancer. In a more specific embodiment, the breast cancer is an intraductal carcinoma. In some embodiments, the hyperproliferative disorder is a metastases of one of the above-mentioned cancers.

The methods and compositions of the present invention can be used to treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79.).

Hyperplasia is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated by the methods and compositions of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In preferred embodiments, the methods and compositions of the invention are used to inhibit growth, progression, and/or metastasis of cancers, in particular those listed above.

In preferred embodiments, the methods and compositions of the present invention can be used to treat, inhibit growth, progression, and/or metastasis of cancers, in particular a cancer selected from the group consisting of breast cancer, ovarian cancer, bladder cancer, prostate cancer, pancreatic cancer, colon cancer, and melanoma.

The antibody or antibodies administered to treat a hyperproliferative disease may optionally be administered with an agent capable of inducing apoptosis. Apoptosis-inducing therapies include chemotherapeutic agents (also known as antineoplastic agents), radiation therapy, and combination radiotherapy and chemotherapy.

In some preferred embodiments, the antibodies of the invention are administered to treat the hyperproliferative disease, for example cancer, are administered with a chemotherapeutic agent. For example, the present invention includes a method of treating cancer comprising administering at least one C35 antibody and at least one HER2 antibody with a therapeutic agent, as well as administering at least one C35 antibody and at least one EGFR antibody with a therapeutic agent.

Exemplary therapeutic agents are vinca alkaloids, epipodophyllotoxins, anthracycline antibiotics, actinomycin D, plicamycin, puromycin, gramicidin D, paclitaxel (Taxol™., Bristol Myers Squibb), colchicine, cytochalasin B, emetine, maytansine, and amsacrine (or "mAMSA"). The vinca alkaloid class is described in Goodman and Gilman's The Pharmacological Basis of Therapeutics (7th ed.), (1985), pp. 1277-1280. Exemplary of vinca alkaloids are vincristine, vinblastine, and vindesine. The epipodophyllotoxin class is described in Goodman and Gilman's The Pharmacological Basis of Therapeutics (7th ed.), (1985), pp. 1280-1281. Exemplary of epipodophyllotoxins are etoposide, etoposide orthoquinone, and teniposide. The anthracycline antibiotic class is described in Goodman and Gilman's The Pharmacological Basis of Therapeutics (7th ed.), (1985), pp. 1283-1285. Exemplary of anthracycline antibiotics are daunorubicin, doxorubicin, mitoxantraone, and bisanthrene. Actinomycin D, also called Dactinomycin, is described in Goodmand and Gilman's The Pharmacological Basis of Therapeutics (7th ed.), (1985), pp. 1281-1283. Plicamycin, also called mithramycin, is described in Goodmand and Gilman's The Pharmacological Basis of Therapeutics (7th ed), (1985), pp.1287-1288. Additional chemotherapeutic agents include cisplatin (Platinol™., Bristol Myers Squibb), carboplatin (Paraplatin™., Bristol Myers Squibb), mitomycin (Mutamycin™., Bristol Myers Squibb), altretamine (Hexalen™, U.S. Bioscience, Inc.), cyclophosphamide (Cytoxan™, Bristol Myers Squibb), lomustine (CCNU) (CeeNU™ Bristol Myers Squibb), carmustine (BCNU) (BiCNU™, Bristol Myers Squibb).

Exemplary chemotherapeutic agents also include aclacinomycin A, aclarubicin, acronine, acronycine, adriamycin, aldesleukin (interleukin-2), altretamine (hexamiethylmelamine), aminoglutethimide, aminoglutethimide (cytadren), aminoimidazole carboxamide, amsacrine (m-AMSA; amsidine), anastrazole (arimidex), ancitabine, anthracyline, anthramycin, asparaginase (elspar), azacitdine, azacitidine (ladakamycin), azaguanine, azaserine, azauridine, 1,1',1"-phosphinothioylidynetris aziridine, azirino(2',3':3,4)pyrrolo (1,2-a)indole-4,7-dione, BCG (theracys), BCNU, BCNU chloroethyl nitrosoureas, benzamide, 4-(bis(2-chloroethyl) amino)benzenebutanoic acid, bicalutamide, bischloroethyl nitrosourea, bleomycin, bleomycin (blenozane), bleomycins, bromodeoxyuridine, broxuridine, busulfan (myleran), carbamic acid ethyl ester, carboplatin, carboplatin (paraplatin), carmustine, carmustine (BCNU; BiCNU), chlorambucil (leukeran), chloroethyl nitrosoureas, chorozotocin (DCNU), chromomycin A3, cis-retinoic acid, cisplatin (cis-ddpl; platinol), cladribine (2-chlorodeoxyadenosine; 2cda; leustatin), coformycin, cycloleucine, cyclophosphamide, cyclophosphamide anhydrous, chlorambucil, cytarabine, cytarabine, cytarabine HCl (cytosar-u), 2-deoxy-2-(((methylnitrosoamino)carbonyl)amino)-D-glucose, dacarbazine, dactinomycin (cosmegen), daunorubicin, Daunorubincin HCl (cerubidine), decarbazine, decarbazine (DTIC-dome), demecolcine, dexamethasone, dianhydrogalactitol, diazooxonorleucine, diethylstilbestrol, docetaxel (taxotere), doxorubicin HCl (adriamycin), doxorubicin hydrochloride, eflomithine, estramustine, estramustine phosphate sodium (emcyt), ethiodized oil, ethoglucid, ethyl carbamate, ethyl methanesulfonate, etoposide (VP16-213), fenretinide, floxuridine, floxuridine (fudr), fludarabine (fludara), fluorouracil (5-FU), fluoxymesterone (halotestin), flutamide, flutamide (eulexin), fluxuridine, gallium nitrate (granite), gemcitabine (gemzar), genistein, 2-deoxy-2-(3-methyl-3-nitrosoureido)-D-glucopyranose, goserelin (zoladex), hexestrol, hydroxyurea (hydra), idarubicin (idamycin), ifosfagemcitabine, ifosfamide (iflex), ifosfamide with mesna (MAID), interferon, interferon alfa, interferon alfa-2a, alfa-2b, alfa-n3, interleukin-2, iobenguane, iobenguane iobenguane, irinotecan (camptosar), isotretinoin (accutane), ketoconazole, 4-(bis(2-chloroethyl) amino)-L-phenylalanine, L-serine diazoacetate, lentinan, leucovorin, leuprolide acetate (LHRH-analog), levamisole (ergamisol), lomustine (CCNU; cee-NU), mannomustine, maytansine, mechlorethamine, mechlorethamine HCl (nitrogen mustard), medroxyprogesterone acetate (provera, depo provera), megestrol acetate (menace), melengestrol acetate, melphalan (alkeran), menogaril, mercaptopurin, mercaptopurine (purinethol), mercaptopurine anhydrous, MESNA, mesna (mesne), methanesulfonic acid, ethyl ester, methotrexate (mtx; methotrexate), methyl-ccnu, mimosine, misonidazole, mithramycin, mitoantrone, mitobronitol, mitoguazone, mitolactol, mitomycin (mutamycin), mitomycin C, mitotane (o,p'-DDD; lysodren), mitoxantrone, mitoxantrone HCl (novantrone), mopidamol, N,N-bis(2-chloroethyl)tetrahydro-2H-1,3,2-oxazaphosphorin-2-amine-2-oxide, N-(1-methylethyl)-4-((2-methylhydrazino)methyl) benzamide, N-methyl-bis(2-chloroethyl)amine, nicardipine, nilutamide (nilandron), nimustine, nitracrine, nitrogen mustard, nocodazole, nogalamycin, octreotide (sandostatin), pacilataxel (taxol), paclitaxel, pactamycin, pegaspargase (PEGx-1), pentostatin (2'-deoxycoformycin), peplomycin, peptichemio, photophoresis, picamycin (mithracin), picibanil, pipobroman, plicamycin, podofilox, podophyllotoxin, porfiromycin, prednisone, procarbazine, procarbazine HCl (matulane), prospidium, puromycin, puromycin aminonucleoside, PUVA (psoralen+ultraviolet a), pyran copolymer, rapamycin, s-azacytidine, 2,4,6-tris(1-aziridinyl)-s-triazine, semustine, showdomycin, sirolimus, streptozocin (zanosar), suramin, tamoxifen citrate (nolvadex), taxon, tegafur, teniposide (VM-26; vumon), tenuazonic acid, TEPA, testolactone, thio-tepa, thioguanine, thiotepa (thioplex), tilorone, topotecan, tretinoin (vesanoid), triaziquone, trichodermin, triethylene glycol diglycidyl ether, triethylenemelamine, triethylenephosphoramide, triethylenethiophosphoramide, trimetrexate (neutrexin), tris(1-aziridinyl)phosphine oxide, tris(1-aziridinyl)phosphine sulfide, tris(aziridinyl)-p-benzoquinone, tris (aziridinyl)phosphine sulfide, uracil mustard, vidarabine, vidarabine phosphate, vinblastine, vinblastine sulfate (velban), vincristine sulfate (oncovin), vindesine, vinorelbine, vinorelbine tartrate (navelbine), (1)-mimosine, 1-(2-chloroethyl)-3-(4-methylcyclohexyl)-1-nitrosourea, (8S-cis)-10-((3-amino-2,3,6-trideoxy-alpha-L-lyxo-hexopyranosyl) oxy)-7,8,9,10-tetrahydro-6,8,11-trihydroxy-8-(hydroxyacetyl)-1-methoxy-5,12-naphthacenedione, 131-meta-iodobenzyl guanidine (I-131 MIBG), 5-(3,3-dimethyl-1-triazenyl)-1H-imidazole-4-carboxamide, 5-(bis(2-chloroethyl)amino)-2,4(1H,3H)-pyrimidinedione, 2,4,6-tris (1-aziridinyl)-s-thiazine, 2,3,5-tris(1-aziridinyl)-2,5-cyclohexadiene-1,4-dione, 2-chloro-N-(2-chloroethyl)-N-methylethanamine, N,N-bis(2-chloroethyl)tetrahydro-2H-1,3,2-oxazaphosphorin-2-amine-2-oxide, 3-deazauridine, 3-iodobenzylguanidine, 5,12-naphthacenedione, 5-azacytidine, 5-fluorouracil, (1aS,8S,8aR,8bS)-6-amino-8-(((aminocarbonyl)oxy)methyl)-1,1a,2,8,8a,8b-hexahydro-8a-methoxy-5-methylazirino(2',3':3,4)pyrrolo(1,2-a)indole-4,7-dione, 6-azauridine, 6-mercaptopurine, 8-azaguanine, and combinations thereof.

In a particular embodiment, the chemotherapeutic agent used in the methods of the present invention is paclitaxel. In another particular embodiment, the chemotherapeutic agent used in the methods of the present invention is adriamycin.

Preferred therapeutic agents and combinations thereof may be administered as an apoptosis-inducing therapy include Doxorubicin and Doxetaxel, Topotecan, Paclitaxel (Taxol), Carboplatin and Taxol, Cisplatin and radiation, 5-fluorouracil (5-FU), 5-FU and radiation, Toxotere, Fludarabine, Ara C, Etoposide, Vincristine, and Vinblastin. In one embodiment, the therapeutic agent is cisplatin.

Chemotherapeutic agents that may be administered in the methods of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, antibodies of the invention are administered in combination with CHOP (cyclophosphamide, doxorubicin, vincristine, and prednisone) or any combination of the components of CHOP.

TABLE 2

Commonly Used Chemotherapy Drugs for Major Cancer Indications

1. Breast cancer: Adjuvant therapy (systemic therapy as an adjunct to or in addition to surgery). Doxorubicin (Adriamycin), cyclophosphamide, and taxanes [paclitaxel (Taxol) and docetaxel (Taxotere)]. These three drugs are also active in metastatic breast cancer but if the patient has already received them as adjuvant therapy the commonly used drugs are capecitabine (Xeloda), gemcitabine (Gemzar), vinorelbine (Navelbine). Commonly prescribed hormonal agents for bone metastases of hormone receptor positive tumors are: tamoxifen and aromatase inhibitors (Arimidex, Femara, Aromasin).
2. Colon cancer: 5-FU plus leucovorin, irinotecan (camptosar), oxaliplatin, and capecitabine.
3. Lung cancer: Cisplatin, carboplatin, paclitaxel, docetaxel, gemcitabine, vinorelbine.
4. Prostate cancer: Docetaxel, estramustine, mitoxantrone (Novantrone), and prednisone.
5. Non-Hodgkin's Lymphoma: Cyclophosphamide, doxorubicin, vincristine (Oncovin), and prednisone.

In some embodiments, the methods of the present invention are directed to administering at least one C35 antibody and at least one HER2 antibody with therapeutic radiation. In other embodiments, the methods are directed to administering at least one C35 antibody and at least one EGFR antibody with therapeutic radiation. Optionally, these methods can also include administration of a chemotherapeutic agent. For example, in some embodiments, the present invention can include administering at least one C35 antibody and at least one HER2 antibody with a chemotherapeutic agent or therapeutic radiation. In other embodiments, the present invention can include administering at least one C35 antibody and at least one EGFR antibody with a chemotherapeutic agent or therapeutic radiation.

Therapeutic radiation includes, for example, fractionated radiotherapy, nonfractionated radiotherapy and hyperfractionated radiotherapy, and combination radiation and chemotherapy. Types of radiation also include ionizing (gamma) radiation, particle radiation, low energy transmission (LET), high energy transmission (HET), ultraviolet radiation, infrared radiation, visible light, and photosensitizing radiation. As used herein, chemotherapy includes treatment with a single chemotherapeutic agent or with a combination of agents. In a subject in need of treatment, chemotherapy may be combined with surgical treatment or radiation therapy, or with other antineoplastic treatment modalities.

In further embodiments, the antibodies of the invention or combinations thereof are administered in combination with an antiviral agent. Antiviral agents that may be administered with the antibodies of the invention include, but are not limited to, acyclovir, ribavirin, amantadine, and remantidine.

Antibodies of the invention or combinations thereof may also be administered with antiemetics such as 2-(ethylthio)-10-(3-(4-methyl-1-piperazinyl) propyl)-10H-phenothiazine (ethylthioperazine), 1-(p-chloro-alpha-phenylbenzyl)-4-(m-methylbenzyl)-piperazine (meclozine, meclizine), etc., and combinations thereof. Polynucleotides and polypeptides of the invention may also be administered with other therapeutic agents, and combinations thereof, disclosed herein or known in the art.

Conventional nonspecific immunosuppressive agents, that may be administered in combination with the antibodies of the invention or combinations thereof include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, antibodies of the invention or combinations thereof are administered in combination with immunosuppressants. Immunosuppressants preparations that may be administered with the antibodies of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, antibodies of the invention are administered alone or in combination with one or more intravenous immune globulin preparations. Intravenous immune globulin preparations that may be administered with the antibodies of the invention include, but not limited to, GAMMAR™, IVEEGAM™, SANDOGLOBULIN™, GAMMAGARD S/D™, and GAMIMUNE™. In a specific embodiment, antibodies of the invention are administered in combination with intravenous immune globulin preparations in transplantation therapy (e.g., bone marrow transplant).

In an additional embodiment, the antibodies of the invention are administered alone or in combination with an anti-inflammatory agent. Anti-inflammatory agents that may be administered with the antibodies of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In an additional embodiment, the antibodies of the invention are administered in combination with cytokines. Cytokines that may be administered with the antibodies of the invention include, but are not limited to, IL2, IL3, IL4, IL5, IL6, IL7, IL10, IL12, IL13, IL15, anti-CD40, CD40L, EN-gamma and TNF-alpha. In another embodiment, antibodies of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the antibodies of the invention are administered in combination with angiogenic proteins. Angiogenic proteins that may be administered with the antibodies of the invention include, but are not limited to, Glioma Derived Growth Factor (GDGF), as disclosed in European Patent Number EP-399816; Platelet Derived Growth Factor-A (PDGF-A), as disclosed in European Patent Number EP-6821 10; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the antibodies of the invention are administered in combination with hematopoietic growth factors. Hematopoietic growth factors that may be administered with the antibodies of the invention include, but are not limited to, LEUKINE™ (SARGRAMOSTIM™) and NEUPOGEN™ (FILGRASTIM™).

In an additional embodiment, the antibodies of the invention are administered in combination with Fibroblast Growth Factors. Fibroblast Growth Factors that may be administered with the antibodies of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Timing of Administration

Any of the apoptosis inducing therapies described herein may be administered before, concurrently with, or after one or more of the anti-C35 antibodies of the present invention. In a particular embodiment, the apoptosis-inducing agent is an antibody selected from an anti-HER2 antibody, an anti-EGFR antibody, and an anti-IGFR antibody. In some embodiments, the anti-C35 antibody and the one or more apoptosis-inducing antibodies are administered concurrently. For example, an anti-C35 antibody is administered concurrently with an anti-HER2 antibody and/or an anti-EGFR antibody, and/or an anti-IGFR antibody. In other embodiments, the antibodies are administered separately. For example, an anti-HER2 antibody could be administered at one time and then an anti-C35 antibody could be administered later the same day or one or more days after the day the first antibody is administered. Likewise, an anti-EGFR antibody could be administered at one time and then an anti-C35 antibody could be administered later the same day or one or more days after the day the first antibody is administered. Likewise, an anti-IGFR antibody could be administered at one time and then an anti-C35 antibody could be administered later the same day or one or more days after the day the first antibody is administered. The anti-C35 antibody could be administered on a day where no other antibodies (e.g., anti-HER2, anti-EGFR, or anti-IGFR) are administered, for example, on a day before administering at least one of an anti-HER2 antibody, an anti-EGR antibody, or an anti-IGFR antibody or a combination thereof, or on a day following the administration of at least one of an anti-HER2 antibody, an anti-EGR antibody, or an anti-IGFR antibody, or a combination thereof.

In other embodiments, administration of multiple antibodies (e.g., an anti-C35 antibody and an anti-HER2 and/or an anti-EGFR antibody and/or an anti-IGFR antibody) may occur before, after, or concurrently with administration of a chemotherapeutic agent, for example, paclitaxel (Taxol™), adriamycin, cisplatin or any other agent described herein. For example, one or two or more of the antibodies could be administered at the same time or on the same day as the paclitaxel, adriamycin, cisplatin, or other agent. Alternatively, the paclitaxel, adriamycin, cisplatin, or other agent could be administered on a day where no antibodies are administered, for example, on a day before administering at least one antibody or on a day following the administration of at least one of the antibodies.

In some embodiments, the apoptosis inducing agent (e.g., the anti-HER2 antibody and/or the anti-EGFR antibody and/or the anti-IGFR antibody) can be administered prior to the administration of the at least one anti-C35 antibody. For example, the apoptosis inducing agent (e.g., the anti-HER2 antibody and/or the anti-EGFR antibody and/or the anti-IGFR antibody) can be administered about 1, 2, 3, 4, 5, 6, 7, 8, 9, 10, 11, 12, 13, 14, 15, 16, 17, 18, 19, 20, 21, 22, 23 or 24 hours before administering at least one antibody to the subject in need of treatment. In some embodiments, the apoptosis inducing agent (e.g., the anti-HER2 antibody and/or the anti-EGFR antibody and/or the anti-IGFR antibody) can be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days before administering at least one of the anti-C35 antibodies of the invention. In particular embodiments, the apoptosis inducing therapy is an antibody, specifically, an anti-HER2 antibody, an anti-EGFR antibody, or an anti-IGFR antibody. In a specific embodiment, the anti-HER2 antibody is trastuzumab. In another specific embodiment, the anti-EGFR antibody is cetuximab. In other embodiments, the apoptosis-inducing agent is a chemotherapeutic agent, for example, paclitaxel or adriamycin or cisplatin.

In some embodiments, the apoptosis inducing agent (e.g., the anti-HER2 antibody and/or the anti-EGFR antibody and/or the anti-IGFR antibody) can be administered after the administration of the at least one anti-C35-antibody. For example, the apoptosis inducing agent (e.g., the anti-HER2 antibody and/or the anti-EGFR antibody and/or the anti-IGFR antibody) can be administered about 1, 2, 3, 4, 5, 6, 7, 8, 9, 10, 11, 12, 13, 14, 15, 16, 17, 18, 19, 20, 21, 22, 23 or 24 hours after administering at least one anti-C35 antibody to the subject in need of treatment. In some embodiments, the apoptosis inducing agent (e.g., the anti-HER2 antibody and/or the anti-EGFR antibody and/or the anti-IGFR antibody) can be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days after administering at least one of the anti-C35 antibodies of the invention. In particular embodiments, the apoptosis inducing therapy is an antibody, specifically, an anti-HER2 antibody, an anti-EGFR antibody, or an anti-IGFR antibody. In a specific embodiment, the anti-HER2 antibody is trastuzumab. In another specific embodiment, the anti-EGFR antibody is cetuximab. In other embodiments, the apoptosis-inducing agent is a chemotherapeutic agent, for example, paclitaxel or adriamycin or cisplatin In one embodiment, the antibodies are administered at weekly intervals during the course of treatment. In a specific embodiment, the antibodies are administered once per week for two weeks during the course of treatment. In a more specific embodiment, the antibodies are administered once per week during the first two weeks of the treatment course. In some embodiments, the antibodies are administered once, twice, or three times per week during a course of treatment. In a specific embodiment, the antibodies are administered twice per week during a course of treatment.

In one embodiment, the antibodies are administered twice weekly. In another embodiment, a therapeutic agent (e.g., a chemotherapeutic agent such as paclitaxel, adriamycin, or cisplatin) is administered once per week. In one embodiment, the therapeutic agent is administered on the first day of treatment and a second dose of the therapeutic agent is administered one week later, while the combination of antibodies is administered twice weekly.

In particular embodiments, a course of treatment can last one week, two weeks, three weeks, four weeks, five weeks, six weeks, seven weeks, eight weeks, one month, two months, three months, four months, five months, six months, seven months, eight months, nine months, ten months, eleven months, or one year. The duration of the course of treatment will depend on the type of cancer, the antibodies used, the chemotherapeutic agent, age of patient, etc. These parameters can be determined by one of skill in the art.

Demonstration of Therapeutic Activity

The methods and antibodies of the invention can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to, cell proliferation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Kits

The present invention provides kits that can be used in the above methods. In one embodiment, a kit comprises at least one C35 and either at least one HER2 antibody or at least one EGFR antibody or at least one IGFR antibody, preferably one or more purified antibodies, in one or more containers.

VIII. Pharmaceutical Compositions and Administration Methods

Methods of preparing and administering one or more of the antibodies of the invention, or antigen-binding fragments, variants, or derivatives thereof of the invention to a subject in need thereof are well known to or are readily determined by those skilled in the art. The route of administration of the antibodies, or antigen-binding fragments, variants, or derivatives thereof may be, for example, oral, parenteral, by inhalation or topical. The term parenteral as used herein includes, e.g., intravenous, intraarterial, intraperitoneal, intramuscular, subcutaneous, rectal or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the antibodies of the invention, or antigen-binding fragments, variants, or derivatives thereof of the invention can be delivered directly to the site of the adverse cellular population thereby increasing the exposure of the diseased tissue to the therapeutic agent.

As previously discussed, at least one anti-C35 antibody and either at least one anti-HER2 antibody or at least one anti-EGFR antibody or at least one anti-IGFR antibody, or antigen-binding fragments, variants, or derivatives thereof of the invention may be administered in a pharmaceutically effective amount for the in vivo treatment of a hyperproliferative disease such as cancer, and in particular, breast cancer.

In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of this application, a pharmaceutically effective amount of an antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

In one embodiment, the entire antibody dose is provided in a single bolus. Alternatively, the dose can be provided by multiple administrations, such as an extended infusion method or by repeated injections administered over a span of hours or days, for example, a span of about 2 to about 4 days.

In some embodiments, the at least one anti-C35 antibody and the at least one anti-HER2 antibody or anti-EGFR antibody or anti-IGFR antibody are administered together in the same pharmaceutical preparation. In other embodiments the antibodies are administered as separate pharmaceutical preparations, either concurrently or sequentially.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. In one example, the determination of a maximum tolerated dose of a chemotherapeutic agent and representative chemotherapy protocols are described in US Pat. Appl. No. 2005/0158323A1 (herein incorporated by reference).

For antibodies, the dosage administered to a patient is typically about 0.1 mg/kg to about 100 mg/kg of the patient's body weight. Preferably, the dosage administered to a patient is between about 0.1 mg/kg and about 20 mg/kg of the patient's body weight, more preferably about 1 mg/kg to about 10 mg/kg of the patient's body weight. In some embodiments the antibodies are administered at a total dose of about 10 mg/kg to about 50mg/kg of the patient's body weight. In another embodiment the antibodies are administered at a total dose of about 20 mg/kg to about 40 mg/kg. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration of the antibodies by modifications such as, for example, lipidation.

As discussed above, the invention also provides a pharmaceutical pack or kit comprising one or more containers filled with one or more of the ingredients of the pharmaceutical compositions of the invention. For example, the pharmaceutical pack or kit may contain the antibody preparation comprising two or more antibodies (e.g., at least one anti-C35 antibody and either at least one anti-HER2 antibody, or at least one anti-EGFR antibody, or at least one anti-IGFR antibody) and the chemotherapeutic agent, such as paclitaxel or adriamycin. In some embodiments, the antibodies are in the same container. In other embodiments, the antibodies are in separate containers. In some embodiments, the chemotherapeutic agent is in the same container as the antibody preparation. In other embodiments, the chemotherapeutic agent is in a separate container. Optionally associated with such container(s) can be a notice in the form prescribed by a governmental agency regulating the manufacture, use or sale of pharmaceuticals or biological products, which notice reflects approval by the agency of manufacture, use or sale for human administration.

Antibodies can be used to assay levels of polypeptides encoded by polynucleotides of the invention in a biological sample using classical immunohistological methods known to those of skill in the art (e.g., see Jalkanen, et al., J. Cell. Biol. 101:976-985 (1985); Jalkanen, et al., J. Cell. Biol. 105: 3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{88}$Re, $^{142}$Pr, $^{105}$Rh, $^{97}$Ru; luminescent labels, such as luminol; and fluorescent labels, such as fluorescein and rhodamine, and biotin.

In addition to assaying levels of polypeptide of the present invention in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $1^{12}$In, $^{99m}$Tc, ($^{131}$I, $^{125}$I, $^{123}$I, $^{121}$I), carbon ($^{14}$C), sulfur (35S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F, $^{153}$Sm, $^{177}$Lu, $^{59}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which express the polypeptide encoded by a polynucleotide of the invention. In vivo tumor imaging is described in S. W. Burchiel et al., "Immunopharmacokinetics of Radiolabeled Antibodies and Their Fragments" (Chapter 13 in Tumor Imaging: The Radiochemical Detection of Cancer, S. W. Burchiel and B. A. Rhodes, eds., Masson Publishing Inc. (1982)).

Techniques known in the art may be applied to label polypeptides of the invention (including antibodies). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No: 4,683,195; Nucleic Acid Hybridization, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical—Immunology* (8th ed.), Appleton & Lange, Norwalk, Conn. (1994) and Mishell and Shiigi (eds), *Selected Methods in Cellular Immunology*, W. H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnol-* ogy 4th ed. Ed. Richard A. Goldsby, Thomas J. Kindt and Barbara A. Osborne, H. Freemand & Co. (2000); Roitt, I., Brostoff, J. and Male D., *Immunology* 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein and herein below, are incorporated herein by reference in their entireties.

EXAMPLES

Example 1

Expression of EGFR and HER2 in C35-Positive Breast Tumors

EGFR and HER2 expression profiles in C35-positive human breast cancer were analyzed. Generally, all HER2-positive tumors are also C35-positive. However, not all C35-positive tumors are HER2-positive. To better understand the clinical profiles of C35-positive tumors, the correlations between C35$^{hi}$ expression by immunohistological score, with HER2 over-expression (HER2$^{hi}$ tumors) and EGFR expression are shown in Table 3. C35$^{hi}$ tumors were defined as score 2+ or 3+.

Tumor Samples

Tumor tissue samples were derived from patients diagnosed with breast cancer who had axillary surgery and no adjuvant therapy and who were lymph node negative on pathology. Three 0.6 mm$^2$ cores of breast cancer tissue were removed from representative tumor areas. These cores were used to construct tissue micro-arrays in triplicate.

Immunohistochemistry

C35 was detected with an affinity purified rabbit polyclonal antibody 78.2 at 0.42 µg/ml. Antigen retrieval was performed using Sodium Citrate buffer (18 µM Citric Acid, 82 µM Sodium Citrate, pH 6.0). Cytokeratins 5/6 (CK5/6) were detected with rabbit polyclonal antibody (Dako, Carpinteria, Calif.) at 1:50 dilution. Antigen retrieval was performed using Tris/EDTA buffer (1 mM EDTA, 10 mM Tris-HCl Base, pH 8.0).

EGFR was detected using mouse antibody (31G7 clone, Invitrogen, Carlsbad, Calif.) with antigen retrieval (0.1% Trypsin, 0.1% Calcium Chloride) at 37° C. for 10 minutes. Standard immunohistochemistry protocol for C35 and EGFR was performed using the REAL EnVision mouse/rabbit kit (Dako), according to manufacturer's instructions.

HER2 immunohistochemistry performed using HercepTest (Dako), according to manufacturer's instructions; with antigen retrieval at 96° C. for 40 minutes. Staining was performed on Autostainer (Dako).

Statistical analysis by Fisher exact two-tailed test showed that within the C35$^{hi}$ group, EGFR expression was significantly different between the HER2$^{hi}$ subset and the HER2$^{-/low}$ subset: p=0.0048.

Thirty (30) C35 positive tumors were scored for expression of Her2/neu and EGFR. Seven (7) out of the 30 tumors were C35+/Her2+/EGFR−, 17/30 are C35+/Her2−/EGFR+, 3/30 are C35+/Her2+/EGFR+ and 3/30 are C35+/Her2−/EGFR−. Ninety percent of the C35 positive tumors were positive for either HER2 or EGFR.

TABLE 3

EGFR Expression in HER2hi and HER2−/low Tumor Tissue Samples

|  | EGFR− | EGFR+ |
|---|---|---|
| HER2−/low | 3 | 17 |
| HER2hi | 7 | 3 |

The results shown in Table 3, above, illustrate that C35 transforming activity is greatest when associated with a second transforming gene.

Example 2

Combination of C35 and HER2 Antibodies for Treating Cancer

Figure 2:
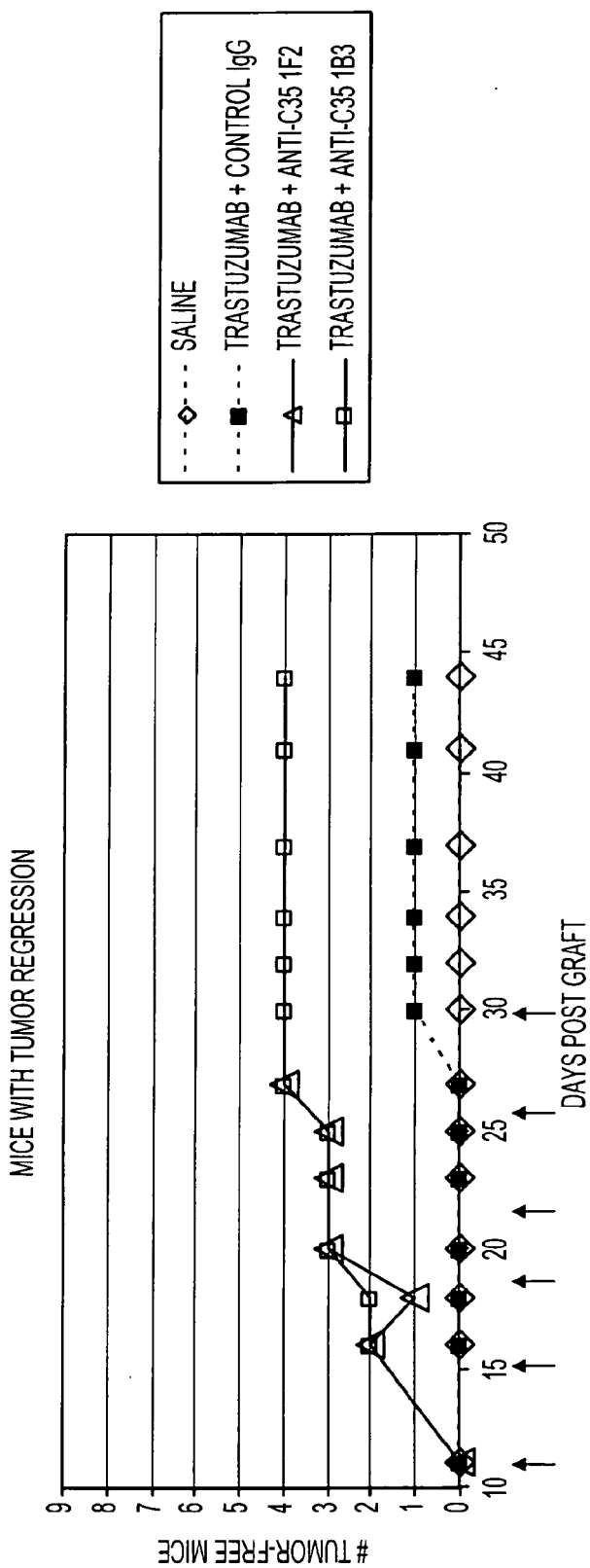
FIG. 2 shows that the number of tumor free mice following BT474-MD xenoengraftment was greater in the group of trastuzumab/anti-C35 combination treated mice (trastuzumab+anti-C35 1F2 or trastuzumab+anti-C35 1B3) compared to mice treated with trastuzumab+Control IgG or Saline. Arrows indicate treatment timepoints.

As illustrated in FIGS. 1 and 2, and described in this example, methods of treating cancer directed to the administration of an anti-C35 antibody and an anti-HER2 antibody were tested. This example shows the effects of anti-C35 mouse monoclonal antibodies, 1F2 and 1B3, in combination with trastuzumab in a naturally Her2+/C35+ human breast cancer xenograft model, BT474-MD.

Production of 1F2 and 1B3 Antibodies

Using 72 hour stock culture, a total of 3.5L of CD Hybridoma was seeded at 2.0×10$^5$ cells/ml. The culture was divided among 3 L shake flasks at 700 ml/flask. The flasks were placed at 37° C. in a 7% CO2 incubator shaking at 90-120 rpm seven days without adding any feed medium. On day 7, a sample was taken from each flask for cell counts prior to harvest. Counts were made by Trypan Blue exclusion. All 3.5L of cell culture was clarified by centrifuging at 3200 rpm (2100×g). Clarified conditioned medium was filter sterilized using 0.22 µm filter units. Pending purification, the clarified/filtered supernatant stored at 4° C. overnight.

For antibody 1B3, supernatants were harvested weekly, approximately 10-12 ml/harvest/factory. Antibody lots consisted of the first 6 consecutive harvests.

Antibody Purification

Antibody in the supernatant was bound to a Gammabind G (GE Healthcare) column. The bound antibody was washed in PBS, pH 7.2 containing 1 M NaCl to reduce endotoxin. The washed antibody was eluted with 0.1M glycine, pH 2.7 into fractions containing 1:5 volume of 1 M Tris, pH 8.0. Fractions containing the eluted antibody were buffer exchanged using G25 PD10 columns (GE Healthcare). The buffer exchanged antibody was pooled and concentrated using Centricon Plus-70 ultrafitration (Millipore, 30 kDA MWCO) to 7.5 mg/mL. The concentrated antibody was passed over anion exchange Mustang Q (Pall) membranes. The flow through containing the antibody was collected. This final formulated antibody was sterile filtered in a biosafety hood using 0.2 um syringe filters (Pall). Protein concentration was determined by A280 using a Nanodrop spectrophotometer.

Cell Culture

The naturally C35+/HER2+ human breast tumor BT474-MD cell line was a generous gift of Ronald Bast at MD Anderson, transferred with permission from Jose Baselga. History of the cell line: BT474 was acquired from ATCC in Jose Baselga's lab, where it was passaged in mice and cultured ex vivo to generate a line that was capable of consistently forming tumors in vivo. The cell line was subcloned by limiting dilution and a clone that had favorable growth kinetics and take rates in vivo was identified. The cell line was designated as BT474-MD, and is cultured in Dulbecco's Modified Eagle Medium (Invitrogen) and adjusted to contain 10% fetal bovine serum. In preparation for grafting, cells were detached with trypsin-EDTA, washed in PBS and resuspended in a volume of $10^8$/ml.

Animals 4 week old Swiss nude mice were purchased from Taconic Farms. Animals were housed under specific pathogen-free, barrier facility conditions. All experiments were performed under University Committee on Animal Resources-approved protocols.

Apoptosis-Inducing Drug

Trastuzumab (Herceptin®, Genentech), an anti-HER2 antibody, was diluted to 21 mg/ml in supplied vehicle. Final dose of trastuzumab was 10 or 100 μg/dose (~0.5 or 5 mg/kg), administered via intravenous injection twice each week for a duration of 3 weeks, starting on day 12 post-graft.

Graft and Treatment

Ten million C35-positive BT474-MD tumor cells were implanted subcutaneously in the mammary fat pads of four-week-old Swiss nude mice. A 90-day release estrogen pellet was implanted in each animal 24 hours prior to graft. Groups of between 6 to 9 mice each received one of the following treatments:

1. No treatment (control group).
2. 10 μg/dose (approximately 0.5 mg/kg) trastuzumab per i.v. injection starting on day 12 and continuing twice weekly for three weeks.
3. 10 μg/dose (approximately 0.5 mg/kg) trastuzumab per i.v. injection, together with 800 μg per i.v. injection (40 mg/kg) of 1F2 murine monoclonal antibody starting on day 12 and continuing twice weekly for three weeks.
4. 10 μg/dose (approximately 0.5 mg/kg) trastuzumab per i.v. injection, together with 800 μg per i.v. injection (40 mg/kg) of 1B3 murine monoclonal antibody starting on day 12 and continuing twice weekly for three weeks.

Average mouse tumor volume was measured at various time points post-graft (FIG. 1). Two measurements were taken with vernier calipers on each tumor; tumor volume was calculated using the formula (length×width$^2$)/2. The percent change in tumor volume was calculated for each tumor as (tumor volume day X/tumor volume day 11)×100. As shown in FIG. 1, trastuzumab administered by itself (with IgG) at the indicated dose without either 1F2 or 1B3 anti-C35 antibody was not as effective at inhibiting tumor growth in mice as trastuzumab administered in combination with an anti-C35 antibody. Each of the two tested murine anti-C35 antibodies, 1F2 and 1B3, in combination with trastuzumab inhibited growth of C35-positive tumors in vivo approximately 5-fold. Furthermore, these combination-treated mice also demonstrated a delay in tumor regression (FIG. 2). Thus, the combination of an anti-C35 antibody with an anti-HER2 antibody had a significant effect in reducing tumor growth.

Example 3

Figure 3B:
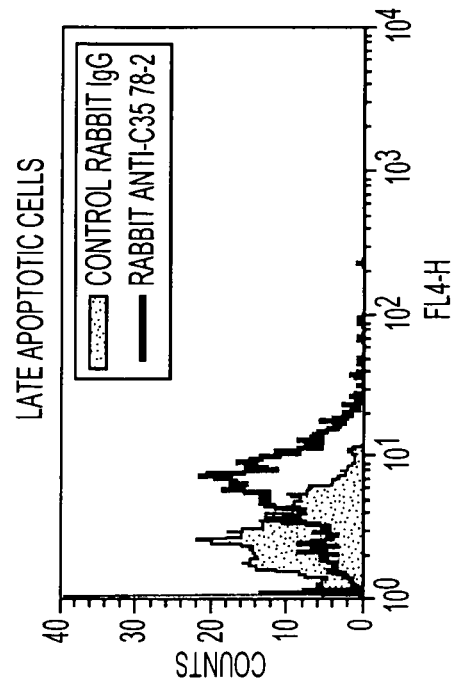
FIG. 3 shows that late-apoptotic (A) trastuzumab-treated BT474 cells stain positive for cell surface anti-C35 antibody staining, while (B) viable cells do not show cell surface anti-C35 antibody staining.
Figure 3A:
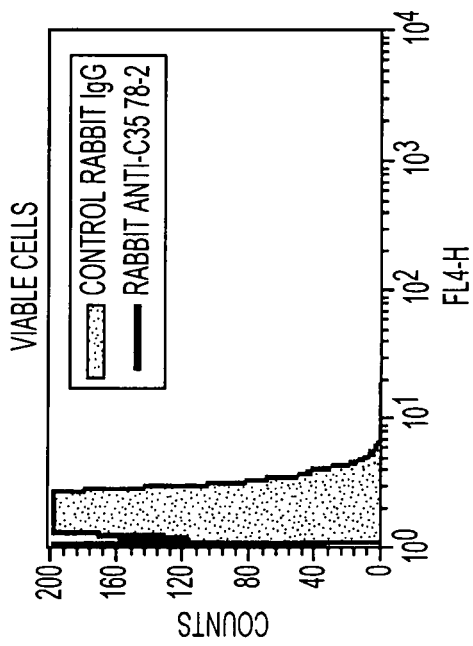

Induction and Scoring of C35 Translocation Following Anti-HER2 Antibody Treatment As illustrated in FIG. 3 and described in this example, an anti-HER2 antibody, trastuzumab, was shown to translocate the C35 protein to the outer cell membrane, where it could be detected by antibody staining. BT474 cells were seeded at 2.5×10$^5$ cells/flask in complete media (Dulbecco's Modified Eagle's Medium+10% Fetal Bovine Serum). Trastuzumab was added to the complete media to a final concentration of 4 ug/ml (37.5 μM). The cells were incubated at 37C for 5 days, then harvested, including floating cells, with trypsin-EDTA.

Antibody Staining:

1 million cells were washed in PAB (Phosphate Buffered Saline, 0.01% Azide, 1% BSA), and incubated for 30 minutes with 0.5 μg rabbit anti-C35 polyclonal antibody 78-2, or rabbit IgG control, followed by donkey anti-rabbit antibody conjugated to Cy5. Cells were washed in 1×Annexin binding buffer, and incubated with 4 μl Annexin-PE (BD Pharmingen, binds phospatidyl serine on apoptotic cells) and 0.1 μM Sytox Green (DNA dye, excluded by live cells) for 15 minutes at room temperature.

FACS Analysis:

Cell populations were gated on FSC/SSC to exclude debris. Samples were then displayed in 2D by AnnexinV/Sytox green staining and gated into the following populations:

a. Viable: AnnexinV−/Sytox Green DNA dye−
b. Early Apoptotic: AnnexinV+/Sytox Green DNA dye−
c. Late Apoptotic: AnnexinV+/Sytox Green DNA dye$^{low}$
d. Dead: AnnexinV+/Sytox Green DNA dye$^{hi}$ Table 4, below, shows that the percentages of trastuzumab-treated BT474 cells that were undergoing apoptosis and/or died were higher than those of untreated cells.

TABLE 4

Percentages of Trastuzumab-Treated BT474 Cells Undergoing Apoptosis

|  | Untreated | Trastuzumab |
| --- | --- | --- |
| Viable | 96.80% | 91.45% |
| Early Apoptotic | 0.24 | 0.65 |
| Late Apoptotic | 0.91 | 2.91 |
| Dead | 1.73 | 4.28 |

As shown in FIG. 3, the population of viable BT474 cells was negative for anti-C35 antibody staining (panel A), while late apoptotic cells were positive for anti-C35 antibody staining (panel B). As discussed herein above, the C35 antigen that is normally associated with internal cell membranes becomes exposed on the surface membrane of tumor cells that have been induced to undergo apoptosis by radiation and/or chemotherapy. See US Appl. Publ. No. 2005/0158323 A1, FIGS. 1-3. As shown in Table 4, trastuzumab treatment increased the population of late apoptotic cells, and late apoptotic cells stained positive for C35. Therefore, trastuzumab can induce apoptosis and translocate the C35 protein to the outer surface of the cell membrane, making it an accessible target for anti-C35 antibodies. Thus, one advantage of combination treatment with anti-HER2 antibody and C35 antibody is that anti-HER2 antibody also induces apoptosis and translocates C35 to the outer tumor cell membrane.

Example 4

Figure 4:
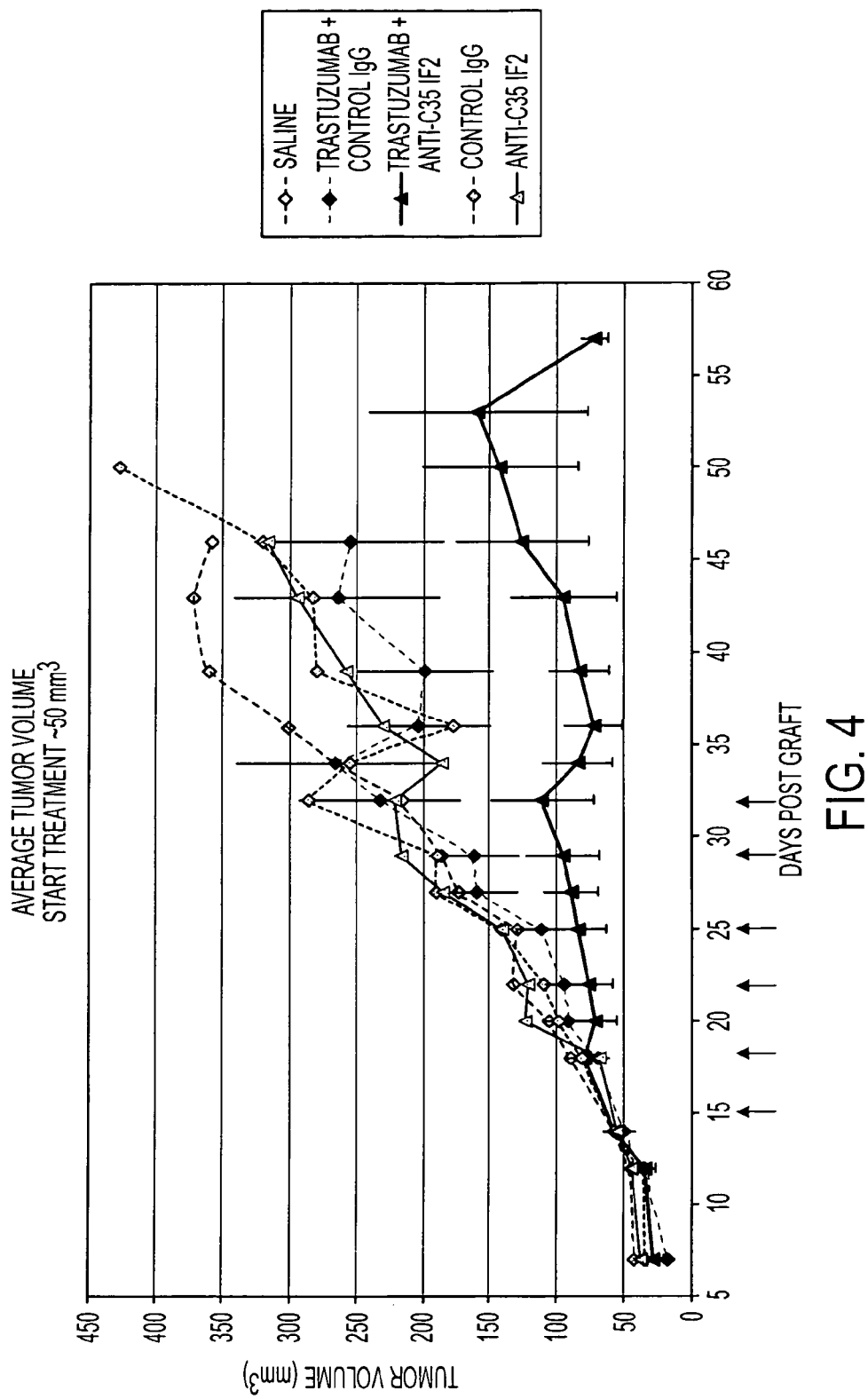
FIG. 4 shows the average tumor volume in BT474-MD-grafted mice treated with trastuzumab+Control IgG, trastuzumab+anti-C35 1F2, Control IgG, anti-C35 1F2, or Saline (treatment starting 15 days post-graft, when the average tumor volume was about 50 mm$^3$). Combination of trastuzumab and anti-C35 1F2 significantly reduced tumor volume compared to 1F2 anti-C35 antibody alone or trastuzumab alone. Arrows indicate treatment timepoints.
Figure 5:
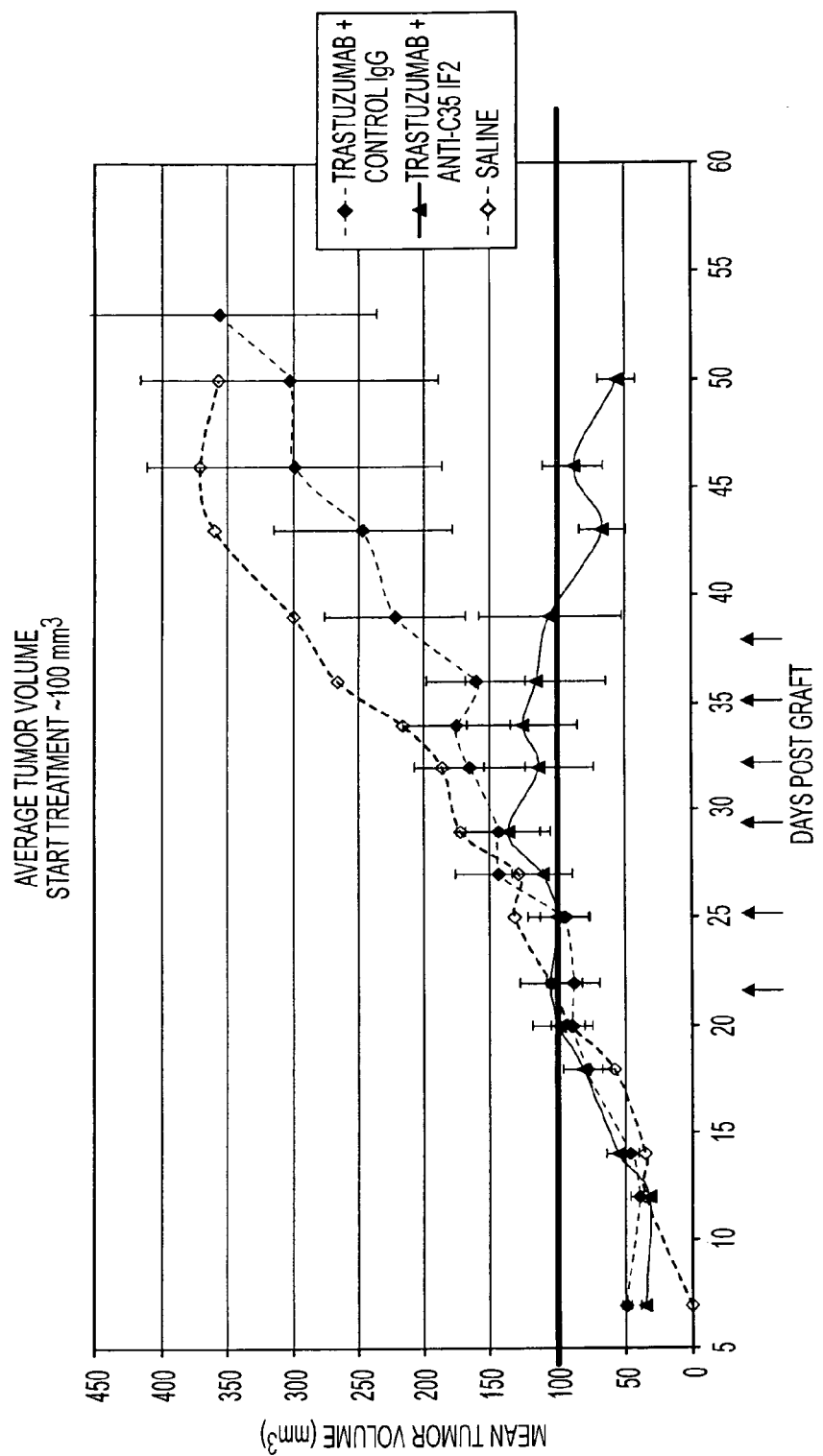
FIG. 5 shows the average tumor volume in BT474-MD-grafted mice treated with trastuzumab+Control IgG or no treatment (Saline) compared to trastuzumab+anti-C35 1F2 (treatment starting 22 days post-graft, when the average tumor volume was about 100 mm$^3$). Combination of trastuzumab and 1F2 anti-C35 antibody significantly reduced tumor volume compared to trastuzumab alone. Arrows indicate treatment timepoints.

C35 Antibody in Combination with HER2 Antibody for Treating Relatively Large Tumors As illustrated in FIGS. 4 and 5, and described in this example, administration of an anti-C35 antibody in combination with an anti-HER2 antibody to BT474-MD-grafted mice stalls or inhibits tumor growth of relatively large tumors. The use of 1F2 anti-C35 antibody alone and in combination with trastuzumab to stall or reduce tumor growth when the treatment was started at a tumor size of about 50 mm$^3$ is shown in FIG. 4. FIG. 5 shows that anti-C35 mouse monoclonal antibody, 1F2, in combination with trastuzumab inhibits the growth of tumors even when the tumor size is larger, about 100 mm$^3$, at the time treatment is started.

The average tumor volume in mice treated with trastuzumab alone, 1F2 alone, or trastuzumab in combination with 1F2 was tested. The methods for determining average tumor volume were similar to the methods described in Example 2, except that in this example treatment started on day 15 or 22, when the average tumor size was about 50 mm³ or 100 mm³, respectively.

For the treatment starting at day 15, groups of between 9 and 12 mice each received one of the following treatments:
1. No treatment (Saline control group).
2. 10 μg/dose (approximately 0.5 mg/kg) trastuzumab per i.v. injection starting on day 15 and continuing twice weekly for about two weeks.
3. 10 μg/dose (approximately 0.5 mg/kg) trastuzumab per i.v. injection, together with 800 μg per i.v. injection (40 mg/kg) of 1F2 murine monoclonal antibody starting on day 15 and continuing twice weekly for about two weeks.
4. Control IgG alone.
5. 800 μg per i.v. injection (40 mg/kg) of 1F2 murine monoclonal antibody starting on day 15 and continuing twice weekly for about two weeks.

For the treatment starting at day 22, groups of between 7 and 12 mice each received the following treatments:
1. No treatment (Saline control group).
2. 10 μg/dose (approximately 0.5 mg/kg) trastuzumab per i.v. injection starting on day 22 and continuing twice weekly for about two weeks.
3. 10 μg/dose (approximately 0.5 mg/kg) trastuzumab per i.v. injection, together with 800 μg per i.v. injection (40 mg/kg) of 1F2 murine monoclonal antibody starting on day 22 and continuing twice weekly for about two weeks.

Average mouse tumor volume was measured at various time points post-graft (FIG. 4). At the start of treatment at day 15, tumor volume was approximately 50mm³. Average tumor volume was measured out to at least 45 days post-graft. As shown in FIG. 4, combinations of trastuzumab and 1F2 anti-C35 antibody reduced growth in tumor volume compared to trastuzumab, 1F2 anti-C35 antibody alone, IgG alone, and untreated.

The use of 1F2 anti-C35 antibody in combination with trastuzumab to reduce tumor growth was also effective for stalling or reducing tumor growth when at the start of treatment, tumor volume was approximately 100 mm³. Average mouse tumor volume was measured at various time points post-graft (FIG. 5). Combinations of trastuzumab and 1F2 anti-C35 antibody stalled or reduced tumor volume compared to trastuzumab alone or untreated.

Table 5, below, shows that the combination of anti-C35 antibody and anti-HER2 antibody was also more effective at preventing tumor growth compared to anti-HER2 antibody alone. As shown in Table 5, the percentage of mice with static tumors, i.e., tumors that failed to grow or remained relatively constant from the beginning of the treatment until the end of the study, was increased with the combination of 1F2 anti-C35 antibody and trastuzumab treatment compared to the anti-C35 1F2 or trastuzumab alone. The increase was shown whether treatment started at 15 days (tumor volume approximately 50 mm³) or whether treatment started at 22 days (tumor volume approximately 100 mm³).

TABLE 5

Comparision of Tumor Size Following Treatment

|  | Static Tumor | Total Mice | % |
| --- | --- | --- | --- |
| Day 15 Treatment | | | |
| trastuzumab + mouse IgG | 2 | 9 | 22% |
| trastuzumab + 1F2 | 8 | 9 | 89% |
| mouse IgG | 0 | 9 | 0% |
| 1F2 | 1 | 9 | 11% |
| Day 22 Treatment | | | |
| trastuzumab + mouse IgG | 2 | 7 | 29% |
| trastuzumab + 1F2 | 9 | 11 | 82% |

Thus, this example shows that the combination of anti-C35 antibody and anti-HER2 antibody was more effective at inhibiting average tumor growth compared to anti-HER2 antibody alone, or anti-C35 antibody alone regardless of whether treatment started at 15 days (tumor volume approximately 50 mm³) or whether treatment started at 22 days (tumor volume approximately 100 mm³). Thus, this example and the examples above show that combined anti-C35 and anti-HER2 treatment was more effective at inhibiting or stalling tumor growth of relatively small and large tumors than either treatment alone.

The entire disclosure of all publications (including patents, patent applications, journal articles, laboratory manuals, books, or other documents) cited herein are hereby incorporated by reference.

What is claimed is:

1. A method of killing cancer cells that express C35 and HER2, said method comprising administering to said cells: (a) an amount of an anti-C35 antibody or antigen binding fragment thereof that specifically binds C35; and (b) an amount of trastuzumab, wherein said amount of anti-C35 antibody and said amount of said trastuzumab is effective for killing said cancer cells.

2. The method of claim 1 further comprising (c) administering an amount of a therapeutic agent.

3. The method of claim 2, wherein said therapeutic agent is a chemotherapeutic agent.

4. The method of claim 3, wherein said chemotherapeutic agent is selected from the group consisting of cisplatin, carboplatin, paclitaxel, adriamycin, docetaxel, taxotere, gemcitabine, and vinorelbine.

5. The method of claim 2, wherein said therapeutic agent is administered prior to administering at least one of said anti-C35 antibody and said trastuzumab.

6. The method of claim 2, wherein said therapeutic agent is administered after administering at least one of said anti-C35 antibody and said trastuzumab.

7. The method of claim 2, wherein said therapeutic agent is administered concurrently with at least one of said anti-C35 antibody and said trastuzumab.

8. The method of claim 1, wherein said anti-C35 antibody is selected from the group consisting of 1F2, 1B3, MAbc0009, MAb 163, MAb 165, MAb 171, antigen binding fragments, variants and derivatives thereof that retain the binding specificity for C35, and any combination thereof.

9. The method of claim 8, wherein said anti-C35 antibody is 1F2 or a variant or derivative thereof that retains binding specificity for C35.

10. The method of claim 9, wherein said anti-C35 antibody is 1F2.

11. The method of claim 1, wherein said cancer cells are selected from the group consisting of breast cancer cells, liver cancer cells, ovarian cancer cells, bladder cancer cells, lung cancer cells, prostate cancer cells, pancreatic cancer cells, colon cancer cells, and melanoma cells.

12. The method of claim 11, wherein said cancer cells are breast cancer cells.

13. The method of claim 1, wherein said anti-C35 antibody and said trastuzumab are administered concurrently.

14. The method of claim 1, wherein said anti-C35 antibody and said trastuzumab are administered sequentially.

* * * * *